(12) United States Patent
Culbert et al.

(10) Patent No.: US 9,713,486 B2
(45) Date of Patent: Jul. 25, 2017

(54) METHOD AND APPARATUS FOR SPINAL FIXATION

(71) Applicant: DePuy Synthes Products, Inc., Raynham, MA (US)

(72) Inventors: Brad S. Culbert, Rancho Santa Margarita, CA (US); Bruce E. Stevens, Laguna Niguel, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 14/574,859

(22) Filed: Dec. 18, 2014

(65) Prior Publication Data

US 2015/0257806 A1 Sep. 17, 2015

Related U.S. Application Data

(63) Continuation of application No. 13/334,644, filed on Dec. 22, 2011, now Pat. No. 8,945,190, which is a
(Continued)

(51) Int. Cl.
*A61B 17/88* (2006.01)
*A61B 17/86* (2006.01)
(Continued)

(52) U.S. Cl.
CPC .............. *A61B 17/86* (2013.01); *A61B 17/70* (2013.01); *A61B 17/7064* (2013.01);
(Continued)

(58) Field of Classification Search
CPC .... A61B 17/56; A61B 17/683; A61B 17/7076
See application file for complete search history.

(56) References Cited

U.S. PATENT DOCUMENTS 2,077,804 A 4/1937 Morrison
2,121,193 A 6/1938 Hanicke
(Continued)

FOREIGN PATENT DOCUMENTS

DE 198 32 798 11/1999
EP 0 525 352 A1 2/1993
(Continued)

OTHER PUBLICATIONS

Apr. 13, 2006 International Search Report for App. No. PCT/US2005/044321.
(Continued)

*Primary Examiner* — Anu Ramana
(74) *Attorney, Agent, or Firm* — Baker & Hostetler LLP

(57) ABSTRACT

Disclosed is a fixation device for spinal fixation. The fixation device includes an elongated body comprising a bone anchor at a distal end. An axially moveable proximal anchor is carried by the proximal end of the fixation device. In one embodiment, the device is inserted through a first vertebra and the bone anchor is rotated into positioned within a second vertebra. The proximal anchor is distally advanced with respect to the bone anchor to provide compression across the first and second vertebra. In other embodiments, the device is used to secure stabilization devices across two or more vertebra.

20 Claims, 22 Drawing Sheets

Related U.S. Application Data continuation of application No. 11/623,290, filed on Jan. 15, 2007, now Pat. No. 8,109,977, which is a continuation of application No. 10/623,193, filed on Jul. 18, 2003, now Pat. No. 7,824,429.

(60) Provisional application No. 60/424,055, filed on Nov. 5, 2002, provisional application No. 60/397,588, filed on Jul. 19, 2002.

(51) Int. Cl.
*A61B 17/70* (2006.01)
*A61B 17/04* (2006.01)
*A61B 17/80* (2006.01)
*A61B 17/68* (2006.01)
*A61B 90/00* (2016.01)

(52) U.S. Cl.
CPC ...... *A61B 17/8685* (2013.01); *A61B 17/0401* (2013.01); *A61B 17/701* (2013.01); *A61B 17/7007* (2013.01); *A61B 17/7049* (2013.01); *A61B 17/8047* (2013.01); *A61B 2017/044* (2013.01); *A61B 2017/0414* (2013.01); *A61B 2017/0424* (2013.01); *A61B 2017/0425* (2013.01); *A61B 2017/0438* (2013.01); *A61B 2017/681* (2013.01); *A61B 2090/037* (2016.02)

(56) References Cited

U.S. PATENT DOCUMENTS

| | | |
|---|---|---|
| 2,485,531 A | 10/1949 | Dzus et al. |
| 2,489,870 A | 11/1949 | Dzus |
| 2,570,465 A | 10/1951 | Lundholm |
| 3,489,143 A | 1/1970 | Holloran |
| 3,698,391 A | 10/1972 | Mahony |
| 4,052,988 A | 10/1977 | Doddi et al. |
| 4,175,555 A | 11/1979 | Herbert |
| 4,275,717 A | 6/1981 | Bolesky |
| 4,456,005 A * | 6/1984 | Lichty ............... A61B 17/8685 606/315 |
| 4,463,753 A | 8/1984 | Gustilo |
| 4,532,660 A | 8/1985 | Field |
| 4,632,101 A | 12/1986 | Freedland |
| 4,640,271 A | 2/1987 | Lower |
| 4,667,663 A | 5/1987 | Miyata |
| 4,688,561 A | 8/1987 | Reese |
| 4,721,103 A | 1/1988 | Freedland |
| 4,743,257 A | 5/1988 | Tormala et al. |
| 4,790,304 A | 12/1988 | Rosenberg |
| 4,796,612 A | 1/1989 | Reese |
| 4,827,917 A | 5/1989 | Brumfield |
| 4,873,976 A | 10/1989 | Schreiber |
| 4,898,186 A | 2/1990 | Ikada et al. |
| 4,903,692 A | 2/1990 | Reese |
| 4,917,554 A | 4/1990 | Bronn |
| 4,940,467 A | 7/1990 | Tronzo |
| 4,968,317 A | 11/1990 | Tormala et al. |
| 4,978,334 A | 12/1990 | Toye et al. |
| 4,978,349 A | 12/1990 | Frigg |
| 5,059,193 A | 10/1991 | Kuslich |
| 5,062,849 A | 11/1991 | Schelhas |
| 5,092,891 A | 3/1992 | Kummer et al. |
| 5,098,433 A | 3/1992 | Freedland |
| 5,116,336 A | 5/1992 | Frigg |
| 5,122,133 A | 6/1992 | Evans |
| 5,122,141 A | 6/1992 | Simpson et al. |
| 5,167,663 A | 12/1992 | Brumfield |
| 5,167,664 A | 12/1992 | Hodorek |
| 5,217,462 A | 6/1993 | Asnis et al. |
| 5,234,431 A | 8/1993 | Keller |
| 5,242,447 A | 9/1993 | Borzone |
| 5,246,441 A | 9/1993 | Ross et al. |
| 5,250,049 A | 10/1993 | Michael |
| 5,300,074 A | 4/1994 | Frigg |
| 5,334,184 A | 8/1994 | Bimman |
| 5,364,398 A | 11/1994 | Chapman et al. |
| 5,370,646 A | 12/1994 | Reese et al. |
| 5,370,647 A | 12/1994 | Graber et al. |
| 5,382,248 A | 1/1995 | Jacobson et al. |
| 5,387,213 A | 2/1995 | Breard et al. |
| 5,395,317 A | 3/1995 | Kambin |
| 5,395,371 A | 3/1995 | Miller et al. |
| 5,415,661 A | 5/1995 | Holmes |
| 5,449,359 A | 9/1995 | Groiso |
| 5,452,748 A | 9/1995 | Simmons et al. |
| 5,470,333 A | 11/1995 | Ray |
| 5,496,318 A | 3/1996 | Howland et al. |
| 5,498,265 A | 3/1996 | Asnis et al. |
| 5,501,695 A | 3/1996 | Anspach, Jr. et al. |
| 5,520,690 A | 5/1996 | Errico et al. |
| 5,527,312 A | 6/1996 | Ray |
| 5,536,127 A | 7/1996 | Pennig |
| 5,540,688 A | 7/1996 | Navas |
| 5,545,164 A | 8/1996 | Howland |
| 5,549,610 A | 8/1996 | Russell et al. |
| 5,558,674 A | 9/1996 | Heggeness et al. |
| 5,569,248 A | 10/1996 | Mathews |
| 5,569,548 A | 10/1996 | Koike et al. |
| 5,591,168 A | 1/1997 | Judet et al. |
| 5,609,634 A | 3/1997 | Voydeville |
| 5,626,613 A | 5/1997 | Schmieding |
| 5,628,751 A | 5/1997 | Sander et al. |
| 5,645,599 A | 7/1997 | Samani |
| 5,649,931 A | 7/1997 | Bryant et al. |
| 5,662,683 A | 9/1997 | Kay |
| 5,667,508 A | 9/1997 | Errico et al. |
| 5,669,915 A | 9/1997 | Caspar et al. |
| 5,713,903 A | 2/1998 | Sander et al. |
| 5,720,753 A | 2/1998 | Sander et al. |
| 5,725,541 A | 3/1998 | Anspach, III et al. |
| 5,725,588 A | 3/1998 | Errico et al. |
| 5,728,097 A | 3/1998 | Mathews |
| 5,728,116 A | 3/1998 | Rosenman |
| 5,741,282 A | 4/1998 | Anspach, III et al. |
| 5,772,662 A | 6/1998 | Chapman et al. |
| 5,782,865 A | 7/1998 | Grptz |
| 5,810,821 A | 9/1998 | Vandewalle |
| 5,849,004 A | 12/1998 | Bramlet |
| 5,871,485 A | 2/1999 | Rao et al. |
| 5,893,850 A | 4/1999 | Cachia |
| 5,904,696 A | 5/1999 | Rosenman |
| 5,908,422 A | 6/1999 | Bresina |
| 5,928,235 A | 7/1999 | Friedl |
| 5,928,244 A | 7/1999 | Tovey et al. |
| 5,935,129 A | 8/1999 | McDevitt et al. |
| 5,947,999 A | 9/1999 | Groiso |
| 5,948,000 A | 9/1999 | Larsen et al. |
| 5,954,722 A | 9/1999 | Bono |
| 5,954,747 A | 9/1999 | Clark |
| 5,957,924 A | 9/1999 | Tormala et al. |
| 5,968,044 A | 10/1999 | Nicholson et al. |
| 5,976,139 A | 11/1999 | Bramlet |
| 5,984,927 A | 11/1999 | Wenstrom, Jr. et al. |
| 5,984,966 A | 11/1999 | Kiena et al. |
| 5,989,255 A | 11/1999 | Pepper et al. |
| 5,993,459 A | 11/1999 | Larsen et al. |
| 5,997,538 A | 12/1999 | Asnis et al. |
| 5,997,541 A | 12/1999 | Schenk |
| 6,001,100 A | 12/1999 | Sherman et al. |
| 6,001,101 A | 12/1999 | Augagneur et al. |
| 6,004,327 A | 12/1999 | Asnis et al. |
| 6,005,161 A | 12/1999 | Brekke et al. |
| 6,007,566 A | 12/1999 | Wenstrom, Jr. |
| 6,007,580 A | 12/1999 | Lehto et al. |
| 6,010,513 A | 1/2000 | Tormala et al. |
| 6,015,410 A | 1/2000 | Tormala et al. |
| 6,019,762 A | 2/2000 | Cole |
| 6,022,352 A | 2/2000 | Vandewalle |
| 6,036,701 A | 3/2000 | Rosenman |
| 6,048,342 A | 4/2000 | Zucherman et al. |
| 6,068,648 A | 5/2000 | Cole et al. |
| 6,083,244 A | 7/2000 | Lubbers et al. |

(56) References Cited

U.S. PATENT DOCUMENTS

| | | |
|---|---|---|
| 6,102,914 A | 8/2000 | Bulstra et al. |
| 6,126,661 A | 10/2000 | Faccioli et al. |
| 6,149,669 A | 11/2000 | Li |
| 6,168,595 B1 | 1/2001 | Durham et al. |
| 6,183,472 B1 | 2/2001 | Lutz |
| 6,183,474 B1 | 2/2001 | Bramlet et al. |
| 6,248,108 B1 | 6/2001 | Tormala et al. |
| 6,251,111 B1 | 6/2001 | Barker et al. |
| 6,267,767 B1 | 7/2001 | Strobel et al. |
| 6,287,313 B1 | 9/2001 | Sasso |
| 6,306,136 B1 | 10/2001 | Baccelli |
| 6,319,254 B1 | 11/2001 | Giet et al. |
| 6,355,043 B1 | 3/2002 | Adam |
| 6,361,537 B1 | 3/2002 | Anderson |
| 6,361,538 B1 | 3/2002 | Fenaroli et al. |
| 6,371,989 B1 | 4/2002 | Chauvin et al. |
| 6,379,355 B1 | 4/2002 | Zucherman et al. |
| 6,379,363 B1 | 4/2002 | Herrington et al. |
| 6,423,061 B1 | 7/2002 | Bryant |
| 6,423,067 B1 | 7/2002 | Eisermann |
| 6,440,169 B1 | 8/2002 | Elberg et al. |
| 6,458,134 B1 | 10/2002 | Songer et al. |
| 6,468,277 B1 | 10/2002 | Justin et al. |
| 6,468,309 B1 | 10/2002 | Lieberman |
| 6,485,491 B1 | 11/2002 | Farris et al. |
| 6,485,518 B1 | 11/2002 | Cornwall et al. |
| 6,488,693 B2 | 12/2002 | Gannoe et al. |
| 6,491,714 B1 | 12/2002 | Bennett |
| 6,506,192 B1 | 1/2003 | Gertzman et al. |
| 6,511,481 B2 | 1/2003 | von Hoffmann et al. |
| 6,520,907 B1 | 2/2003 | Foley et al. |
| 6,527,774 B2 | 3/2003 | Lieberman |
| 6,540,747 B1 | 4/2003 | Marino |
| 6,544,265 B2 | 4/2003 | Lieberman |
| 6,547,793 B1 | 4/2003 | McGuire |
| 6,547,795 B2 | 4/2003 | Schneiderman |
| 6,551,319 B2 | 4/2003 | Lieberman |
| 6,551,322 B1 | 4/2003 | Lieberman |
| 6,558,389 B2 | 5/2003 | Clark et al. |
| 6,562,046 B2 | 5/2003 | Sasso |
| 6,562,049 B1 | 5/2003 | Norlander et al. |
| 6,579,293 B1 | 6/2003 | Chandran |
| 6,582,453 B1 | 6/2003 | Tran et al. |
| 6,585,730 B1 | 7/2003 | Foerster |
| 6,585,740 B2 | 7/2003 | Schlapfer et al. |
| 6,589,249 B2 | 7/2003 | Sater et al. |
| 6,599,297 B1 | 7/2003 | Carlsson et al. |
| 6,610,091 B1 | 8/2003 | Reiley |
| 6,613,050 B1 | 9/2003 | Wagner et al. |
| 6,613,051 B1 * | 9/2003 | Luk .................. A61B 17/7049 606/250 |
| 6,626,944 B1 | 9/2003 | Taylor |
| 6,632,224 B2 | 10/2003 | Cachia et al. |
| 6,648,890 B2 | 11/2003 | Culbert et al. |
| 6,648,893 B2 | 11/2003 | Dudasik |
| 6,669,698 B1 | 12/2003 | Tromanhauser et al. |
| 6,669,729 B2 | 12/2003 | Chin |
| 6,673,074 B2 | 1/2004 | Shluzas |
| 6,685,706 B2 | 2/2004 | Padget et al. |
| 6,733,534 B2 | 5/2004 | Sherman |
| 6,752,831 B2 | 6/2004 | Sybert et al. |
| 6,761,720 B1 | 7/2004 | Senegas |
| 6,770,075 B2 | 8/2004 | Howland |
| 6,793,656 B1 | 9/2004 | Mathews |
| 6,796,983 B1 | 9/2004 | Zucherman et al. |
| 6,808,526 B1 | 10/2004 | Magerl et al. |
| 6,835,205 B2 | 12/2004 | Atkinson et al. |
| 6,887,243 B2 | 5/2005 | Culbert et al. |
| 6,890,333 B2 | 5/2005 | von Hoffmann et al. |
| 6,908,465 B2 | 6/2005 | von Hoffman et al. |
| 6,921,403 B2 | 7/2005 | Cragg et al. |
| 6,923,811 B1 | 8/2005 | Carl et al. |
| 6,929,606 B2 | 8/2005 | Ritland |
| 6,942,668 B2 | 9/2005 | Padget et al. |
| 6,945,975 B2 | 9/2005 | Dalton |
| 6,951,561 B2 * | 10/2005 | Warren .................. A61B 17/68 606/328 |
| 7,060,068 B2 | 6/2006 | Tromanhauser et al. |
| 7,070,601 B2 | 7/2006 | Culbert et al. |
| 7,074,203 B1 | 7/2006 | Johanson et al. |
| 7,326,211 B2 | 2/2008 | Padget et al. |
| 7,371,238 B2 | 5/2008 | Soboleski et al. |
| 7,422,594 B2 | 9/2008 | Zander |
| 7,488,326 B2 | 2/2009 | Elliott |
| 7,556,629 B2 | 7/2009 | von Hoffmann et al. |
| 7,625,378 B2 | 12/2009 | Foley |
| 7,648,523 B2 | 1/2010 | Mirkovic et al. |
| 7,699,878 B2 | 4/2010 | Pavlov et al. |
| 7,824,429 B2 | 11/2010 | Culbert et al. |
| 7,846,183 B2 | 12/2010 | Blain |
| 7,857,832 B2 | 12/2010 | Culbert et al. |
| 7,901,438 B2 | 3/2011 | Culbert et al. |
| 7,938,832 B2 | 5/2011 | Culbert et al. |
| 7,993,377 B2 | 8/2011 | Culbert et al. |
| 7,998,176 B2 | 8/2011 | Culbert |
| 8,109,977 B2 | 2/2012 | Culbert et al. |
| 8,715,284 B2 | 5/2014 | Culbert |
| 8,945,190 B2 | 2/2015 | Culbert et al. |
| 2001/0027320 A1 | 10/2001 | Sasso |
| 2002/0143331 A1 | 10/2002 | Zucherman et al. |
| 2003/0028250 A1 | 2/2003 | Reiley et al. |
| 2003/0063582 A1 | 4/2003 | Culbert |
| 2003/0065330 A1 | 4/2003 | Zucherman et al. |
| 2003/0220643 A1 | 11/2003 | Ferree |
| 2003/0229350 A1 | 12/2003 | Kay |
| 2004/0006391 A1 | 1/2004 | Reiley |
| 2004/0049190 A1 | 3/2004 | Biedermann et al. |
| 2004/0097941 A1 | 5/2004 | Weiner et al. |
| 2004/0143734 A1 | 7/2004 | Buer et al. |
| 2004/0186482 A1 | 9/2004 | Kolb et al. |
| 2004/0225292 A1 | 11/2004 | Sasso et al. |
| 2004/0254575 A1 | 12/2004 | Obenchain et al. |
| 2005/0033434 A1 | 2/2005 | Berry |
| 2005/0090833 A1 | 4/2005 | Di Poto |
| 2005/0119657 A1 | 6/2005 | Goldsmith |
| 2005/0137595 A1 | 6/2005 | von Hoffmann et al. |
| 2005/0143734 A1 | 6/2005 | Cachia et al. |
| 2005/0149030 A1 | 7/2005 | Serhan |
| 2005/0216026 A1 | 9/2005 | Culbert |
| 2005/0251142 A1 | 11/2005 | von Hoffmann et al. |
| 2005/0256525 A1 | 11/2005 | Culbert et al. |
| 2005/0283238 A1 | 12/2005 | Reiley |
| 2006/0015105 A1 | 1/2006 | Warren et al. |
| 2006/0030872 A1 | 2/2006 | Culbert et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0058790 A1 | 3/2006 | Carl et al. |
| 2006/0079908 A1 | 4/2006 | Lieberman |
| 2006/0084977 A1 | 4/2006 | Lieberman |
| 2006/0085010 A1 | 4/2006 | Lieberman |
| 2006/0100707 A1 | 5/2006 | Stinson et al. |
| 2006/0195103 A1 | 8/2006 | Padget et al. |
| 2006/0217711 A1 | 9/2006 | Stevens et al. |
| 2008/0108996 A1 | 5/2008 | Padget et al. |
| 2008/0287981 A1 | 11/2008 | Culbert et al. |
| 2009/0069813 A1 | 3/2009 | von Hoffmann et al. |
| 2009/0105745 A1 | 4/2009 | Culbert et al. |
| 2009/0149857 A1 | 6/2009 | Culbert et al. |

FOREIGN PATENT DOCUMENTS

| | | |
|---|---|---|
| EP | 0 625 336 | 11/1994 |
| EP | 1 046 376 A1 | 4/2000 |
| EP | 0 853 929 B1 | 9/2002 |
| EP | 1 374 784 A1 | 1/2004 |
| FR | 2 699 065 | 12/1992 |
| FR | 2 728 778 | 12/1994 |
| FR | 2 745 709 | 3/1996 |
| FR | 2 800 601 | 11/1999 |
| FR | 2 801 189 | 11/1999 |
| FR | 2 808 182 | 4/2000 |

(56) References Cited

FOREIGN PATENT DOCUMENTS

| | | |
|---|---|---|
| GB | 2157788 A | 10/1985 |
| GB | 2173565 A | 10/1986 |
| JP | 64-52439 | 2/1989 |
| JP | 6-319742 A | 11/1994 |
| JP | 07-184922 | 7/1995 |
| JP | 10-085232 A | 4/1998 |
| JP | 11-089854 A | 4/1999 |
| WO | WO 91/09572 | 7/1991 |
| WO | WO 99/62417 | 12/1999 |
| WO | WO 00/67652 | 5/2000 |
| WO | WO 03/043488 | 5/2003 |
| WO | WO 2004/008949 | 1/2004 |
| WO | WO 2004/064603 | 8/2004 |
| WO | WO 2004/078220 | 9/2004 |
| WO | WO 2004/078221 | 9/2004 |
| WO | WO 2004/098453 | 11/2004 |
| WO | WO 2006/017507 | 2/2006 |
| WO | WO 2006/063083 | 6/2006 |
| WO | WO 2006/108067 | 10/2006 |
| WO | WO 2007/124130 | 11/2007 |

OTHER PUBLICATIONS

Apr. 22, 2004 International Search Report for App. No. PCT/US03/23645 filed Jul. 18, 2003.
Apr. 11, 2007 International Search Report for App. No. PCT/US03/23645 filed Jul. 18, 2003.
Apr. 19, 2007 Office Action for European Application No. 02 719 402.6 filed Mar. 29, 2002.
May 27, 2009 Office Action for Japanese Patent Application No. 2005-50552 filed on Jul. 18, 2003.
Aug. 4, 2009 Extended European Search Report received in European Application No. 09164698.4, 5 pages.
Mar. 31, 2010 Office Action for Japanese Patent Application No. 2005-505552 filed on Jul. 18, 2003.
Mar. 23, 2011 Office Action for Japanese Application No. 2005-505552 filed Jul. 18, 2003.
King, M.D. Don, "Internal Fixation for Lumbosacral Fusion", The Journal of Bone and Joint Surgery. J Bone Joint Surg Am. 1948; 30:560-578.

* cited by examiner

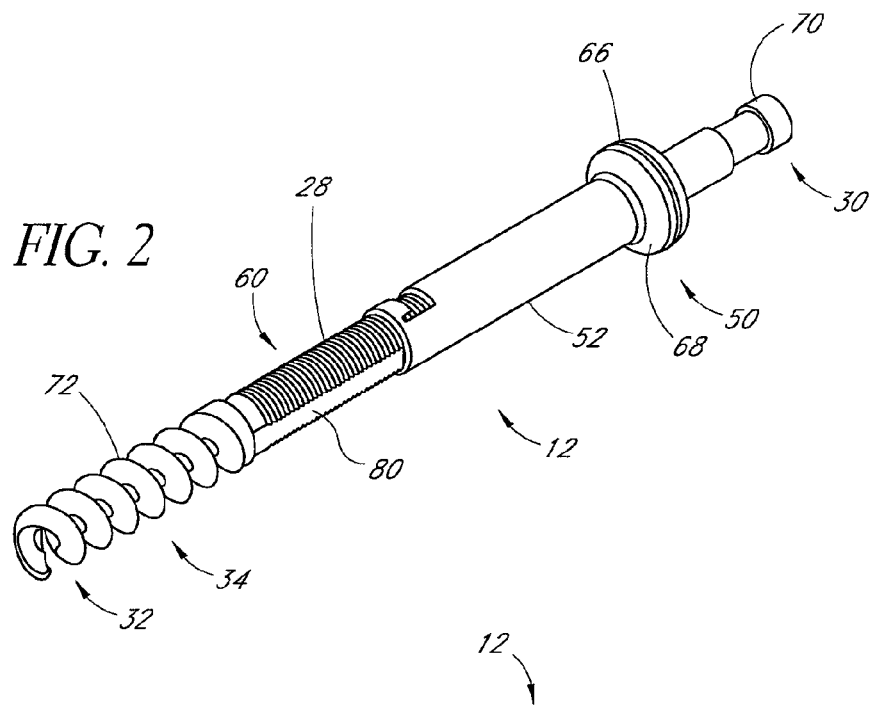
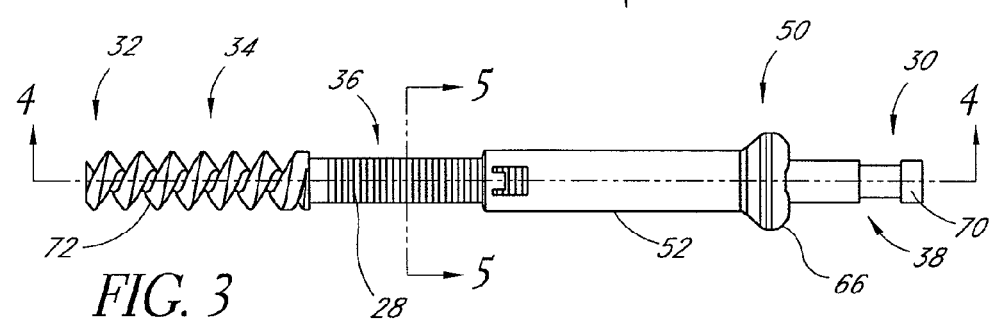
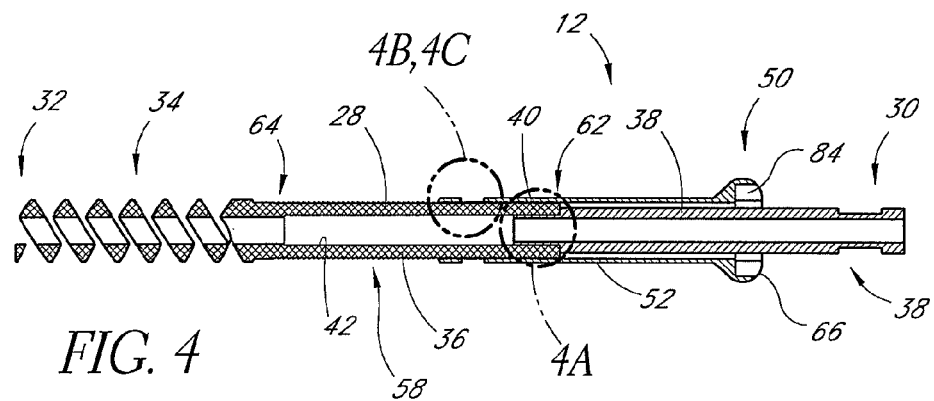

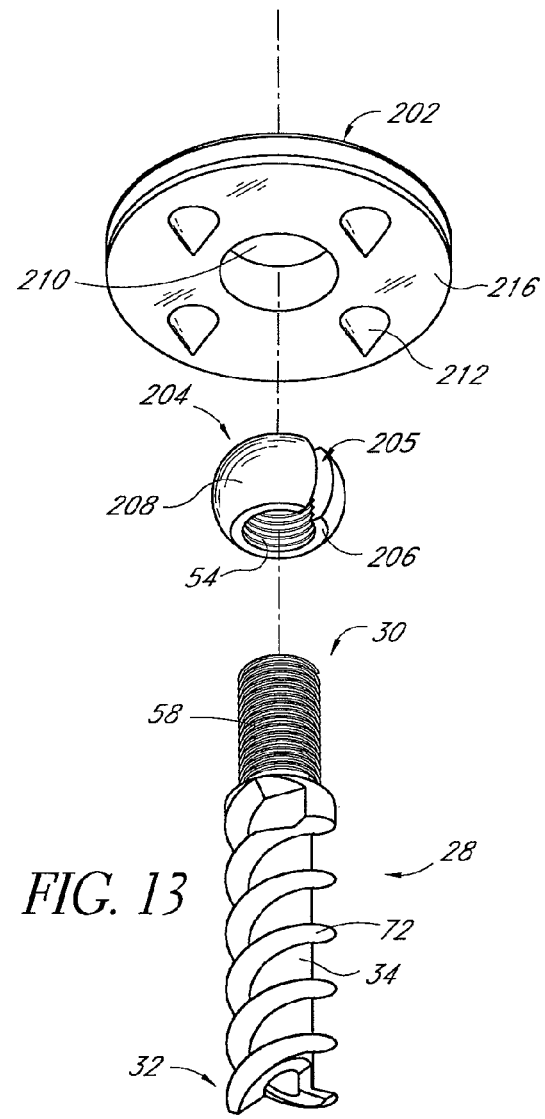
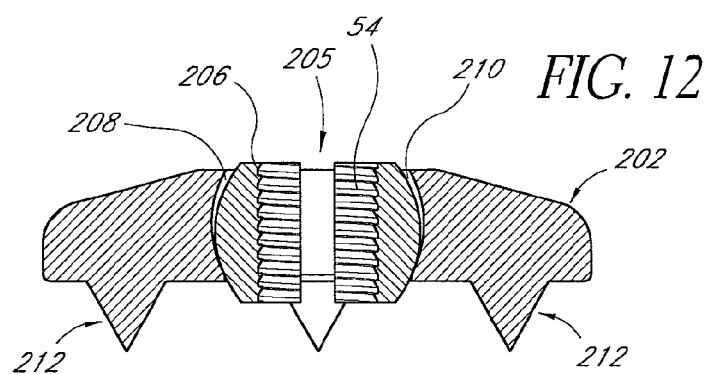
FIG. 13
FIG. 12

METHOD AND APPARATUS FOR SPINAL FIXATION

PRIORITY INFORMATION

This application is a continuation of U.S. patent application Ser. No. 13/334,644, filed Dec. 22, 2011, which is a continuation of U.S. patent application Ser. No. 11/623,290, filed Jan. 15, 2007, now U.S. Pat. No. 8,109,977, which is a continuation of U.S. patent application Ser. No. 10/623, 193, filed Jul. 18, 2003, now U.S. Pat. No. 7,824,429, which claims the priority benefit under 35 U.S.C. §119(e) of Provisional Application 60/397,588 filed Jul. 19, 2002 and Provisional Application 60/424,055 filed Nov. 5, 2002, the entire contents of these applications are hereby incorporated by reference herein.

BACKGROUND OF THE INVENTION

Field of the Invention

The present invention relates to medical devices and, more particularly, to methods and apparatus for spinal stabilization.

Description of the Related Art

The human spine is a flexible weight bearing column formed from a plurality of bones called vertebrae. There are thirty three vertebrae, which can be grouped into one of five regions (cervical, thoracic, lumbar, sacral, and coccygeal). Moving down the spine, there are generally seven cervical vertebra, twelve thoracic vertebra, five lumbar vertebra, five sacral vertebra, and four coccygeal vertebra. The vertebra of the cervical, thoracic, and lumbar regions of the spine are typically separate throughout the life of an individual. In contrast, the vertebra of the sacral and coccygeal regions in an adult are fused to form two bones, the five sacral vertebra which into extend the formation of the sacrum and the four coccygeal vertebra which into the coccyx.

In general, each vertebra contains an anterior, solid segment or body and a posterior segment or arch. The arch is generally formed of two pedicles and two laminae, supporting seven processes—four articular, two transverse, and one spinous. There are exceptions to these general characteristics of a vertebra. For example, the first cervical vertebra (atlas vertebra) has neither a body nor spinous process. Also, the second cervical vertebra (axis vertebra) has an odontoid process, which is a strong, prominent process, shaped like a tooth, rising perpendicularly from the upper surface of the body of the axis vertebra. Further details regarding the construction of the spine may be found in such common references as Gray's Anatomy, Crown Publishers, Inc., 1977, pp. 33-54, which is herein incorporated by reference.

The human vertebrae and associated connective elements are subjected to a variety of diseases and conditions which cause pain and disability. Among these diseases and conditions are spondylosis, spondylolisthesis, vertebral instability, spinal stenosis and degenerated, herniated, or degenerated and herniated intervertebral discs. Additionally, the vertebrae and associated connective elements are subject to injuries, including fractures and torn ligaments and surgical manipulations, including laminectomies.

The pain and disability related to the diseases and conditions often result from the displacement of all or part of a vertebra from the remainder of the vertebral column. Over the past two decades, a variety of methods have been developed to restore the displaced vertebra to their normal position and to fix them within the vertebral column. Such methods typically include various fixation systems that are used for the stabilization of fractures and/or fusions of various portions of the spine. These fixation systems may include a variety of longitudinal elements such as rods or plates which span two or more vertebra and are affixed to the vertebra by various fixation elements such as wires, staples, and screws (often inserted through the pedicles of the vertebra). These systems may be affixed to either the posterior or the anterior side of the spine. In other applications, one or more bone screws may be inserted through adjacent vertebrae to provide stabilization.

Notwithstanding the variety of efforts in the prior art, there remains a need for an orthopedic fixation device for spinal fixation with improved locking force, which resists migration and rotation, and which can be easily and rapidly deployed within the spine.

SUMMARY OF THE INVENTION

There is provided in accordance with one aspect of the present invention, a method of providing compression across two vertebra. The method comprises advancing a fixation device having a distal portion with a bone anchor and a proximal portion through a portion of a first vertebra and positioning the bone anchor into a second vertebra. A proximal anchor is axially advanced to provide compression across the two vertebra. In one embodiment, the bone anchor is rotated to secure the fixation device to the first vertebra. In other embodiments, the fixation device is advanced through the inferior facet of a superior vertebra and into the base of the transverse process of the immediately inferior vertebra. In other embodiments, the fixation device is advanced through the inferior facet of a superior vertebra and into the base of the facet or pedicle of the immediately inferior vertebra. These methods may additionally comprise the step of uncoupling the first portion from the second portion, such as for device removal following fusion. In addition, the method may include repeating some of these steps to provide bilateral symmetry.

There is provided in accordance with one aspect of the present invention, a method of providing compression across two vertebra. The method comprises advancing a fixation device having a distal portion with a bone anchor and a proximal portion through a portion of a first vertebra and positioning the bone anchor into a second vertebra, the fixation device may be advanced through an aperture on an implantable support structure such as a plate, a rod or a cage, and anchored into a vertebral body to attach the support structure to the vertebral body.

In accordance with another embodiment of the present invention, a spinal fixation device comprises an elongate body, having a proximal end and a distal end; a distal anchor on the distal end; a retention structure on the body, proximal to the distal anchor; and a proximal anchor, moveably carried by the body. At least one complementary retention structure is provided on the proximal anchor and is configured to permit proximal movement of the body with respect to the proximal anchor but resist distal movement of the body with respect the proximal anchor. A flange is configured to receive the proximal anchor, The proximal anchor and the flange having complementary surface structures to permit angular adjustment with respect to the longitudinal axis of the proximal anchor and the body and the longitudinal axis of the flange.

In accordance with another embodiment of the present invention, a method of providing spinal fixation comprises the steps of advancing a fixation device that comprises a body having a first portion that forms a bone anchor and a second portion that forms a proximal end; through a portion of a first vertebra, advancing the bone anchor of the fixation device into a second vertebra, advancing a proximal anchor distally along the fixation device; and distally advancing proximal anchor with respect to the body to adjust compression across the first and second vertebrae.

In accordance with another embodiment of the present invention, a method of providing spinal fixation comprises the steps of advancing a first fixation device that comprises a body having a first portion that forms a distal bone anchor and a second portion that forms a proximal end into a first vertebra, advancing a second fixation device that comprises a body having a first portion that forms a distal bone anchor and a second portion that forms a proximal end into a second vertebra, coupling a first portion of a fixation structure to the first fixation device, coupling a second portion of the fixation structure to the second fixation device, securing the first fixation structure to the first vertebra by advancing a first proximal anchor distally along the body of the first fixation device and proximally retracting the proximal anchor with respect to the body; and securing the second fixation structure to the second vertebra by advancing a second proximal anchor distally along the body of the second fixation device and proximally retracting the second proximal anchor with respect to the body.

Further features and advantages of the present invention will become apparent to those of skill in the art in view of the detailed description of preferred embodiments which follows, when considered together with the attached drawings and claims.

BRIEF DESCRIPTION OF THE DRAWINGS

FIG. 2 is a side perspective view of an exemplary fixation device similar to that of FIG. 1.

FIG. 3 is a side elevational view of the fixation device of FIG. 2.

FIG. 4 is a cross-sectional view taken through line 4-4 of FIG. 3.

FIG. 12 is a cross-sectional view of the flange and proximal anchor of the bone fixation device of FIG. 11.

FIG. 13 is an unassembled bottom perspective view of the bone fixation device of FIG. 9.

DETAILED DESCRIPTION OF THE PREFERRED EMBODIMENTS

Although the fixation devices of the present invention will be disclosed primarily in the context of a spinal fixation procedure, the methods and structures disclosed herein are intended for application in any of a variety medical applications, as will be apparent to those of skill in the art in view of the disclosure herein. For example, the bone fixation device may be applicable to proximal fractures of the femur and a wide variety of fractures and osteotomies, the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. See e.g., U.S. Pat. No. 6,511,481, which is hereby incorporated by reference herein. A wide variety of phalangeal and metatarsal osteotomies and fractures of the foot may also be stabilized using the bone fixation devices described herein. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. Fractures of the fibular and tibial malleoli, pilon fractures and other fractures of the bones of the leg may be fixated and stabilized with these bone fixation devices with or without the use of plates, both absorbable or non-absorbing types, and with alternate embodiments of the current invention The fixation devices may also be used to attach tissue or structure to the bone, such as in ligament reattachment and other soft tissue attachment procedures. Plates and washers, with or without tissue spikes for soft tissue attachment, and other implants may also be attached to bone, using either resorbable or nonresorbable fixation devices depending upon the implant and procedure. The fixation devices may also be used to attach sutures to the bone, such as in any of a variety of tissue suspension procedures. The bone fixation device described herein may be used with or without plate(s) or washer(s), all of which can be either permanent, absorbable, or combinations.

Figure 1:
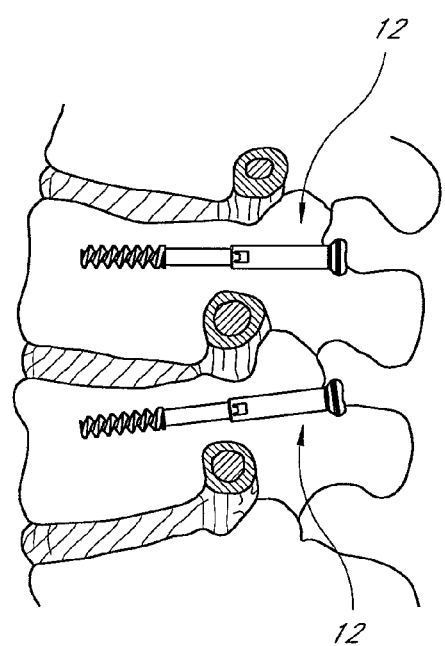
FIG. 1 a side elevational view of a portion of a vertebra having a exemplary embodiment of a fixation device implanted therein.

Referring to FIG. 1, there as illustrated a side elevational view of an exemplary embodiment of a bone fixation device 12. In FIG. 1, a pair of fixation devices 12 are positioned within adjacent vertabrae 10. As will be explained in more detail below, the bone fixation device 12 may be used in a variety of techniques to stabilize the spine. For example, the bone fixation devices 12 may be used as pedicle or facet screws that may be unilaterally or bilaterally symmetrically mounted on adjacent or non-adjacent vertebrae and used in combination one or more linkage rods or plates to facilitate fusion of one or more vertebrae. The bone fixation devices 12 disclosed herein may also be used as a fixation screw to secure two adjacent vertebra to each other in a trans-laminar, trans-facet or facet-pedicle (e.g., the Boucher technique) applications. One of skill of the art will also recognize that the bone fixation devices disclosed herein may be used for posterior stability after laminectomy, artificial disc replacement, repairing odontoid fractures and other fractures of the spine, and other applications for providing temporary or permanent stability in the spinal column.

Referring to FIGS. 2-4, the exemplary fixation device 12 will now be described in detail. The fixation device 12 comprises a body 28 that extends between a proximal end 30 and a distal end 32. The length, diameter and construction materials of the body 28 can be varied, depending upon the intended clinical application. In embodiments optimized for spinal fixation in an adult human population, the body 28 will generally be within the range of from about 20-90 mm in length and within the range of from about 3.0-8.5 mm in maximum diameter. The length of the helical anchor, discussed below, may be about 8-80 millimeters. Of course, it is understood that these dimensions are illustrative and that they may be varied as required for a particular patient or procedure.

In one embodiment, the body 28 comprises titanium. However, as will be described in more detail below, other metals or bioabsorbable or nonabsorbable polymeric materials may be utilized, depending upon the dimensions and desired structural integrity of the finished fixation device 12.

The distal end 32 of the body 28 is provided with a cancellous bone anchor or distal cortical bone anchor 34. Generally for spinal fixation, the distal bone anchor 34 is adapted to be rotationally inserted into a portion (e.g., the facet or pedicle) of a first vertebra. In the illustrated embodiment, the distal anchor 34 comprises a helical locking structure 72 for engaging cancellous and/or distal cortical bone. In the illustrated embodiment, the locking structure 72 comprises a flange that is wrapped around an axial lumen. The flange extends through at least one and generally from about two to about 50 or more full revolutions depending upon the axial length of the distal anchor and intended application. The flange will generally complete from about 2 to about 20 revolutions. The helical flange 72 is preferably provided with a pitch and an axial spacing to optimize the retention force within cancellous bone, to optimize compression.

The helical flange 72 of the illustrated embodiment has a generally triangular cross-sectional shape (see FIG. 4). However, it should be appreciated that the helical flange 72 can have any of a variety of cross sectional shapes, such as rectangular, oval or other as deemed desirable for a particular application through routine experimentation in view of the disclosure herein. The outer edge of the helical flange 72 defines an outer boundary. The ratio of the diameter of the outer boundary to the diameter of the central lumen can be optimized with respect to the desired retention force within the cancellous bone and giving due consideration to the structural integrity and strength of the distal anchor 34. Another aspect of the distal anchor 34 that can be optimized is the shape of the outer boundary and the central core, which in the illustrated embodiment are generally cylindrical.

The distal end 32 and/or the outer edges of the helical flange 72 may be atraumatic (e.g., blunt or soft). This inhibits the tendency of the fixation device 12 to migrate anatomically distally and potentially out of the vertebrae after implantation. Distal migration is also inhibited by the dimensions and presence of a proximal anchor 50, which will be described below. In the spinal column, distal migration is particularly disadvantageous because the distal anchor may harm the tissue, nerves, blood vessels and spinal cord which lie within and/or surround the spine.

A variety of other arrangements for the distal anchor 32 can also be used. For example, the various distal anchors described in co-pending U.S. patent application Ser. No. 10/012,687, filed Nov. 13, 2001 can be incorporated into the fixation device 12 described herein. The entire contents of this application is hereby expressly incorporated by reference. In particular, the distal anchor may comprise a single helical thread surrounding a central core, much as in a conventional screw, which has been cannulated to facilitate placement over a wire. Alternatively, a double helical thread may be utilized, with the distal end of the first thread rotationally offset from the distal end of the second thread. The use of a double helical thread can enable a greater axial travel for a given degree of rotation and greater retention force than a corresponding single helical thread. Specific distal anchor designs can be optimized for the intended use, taking into account desired performance characteristics, the integrity of the distal bone, and whether the distal anchor is intended to engage exclusively cancellous bone or will also engage cortical bone.

Figure 4A:
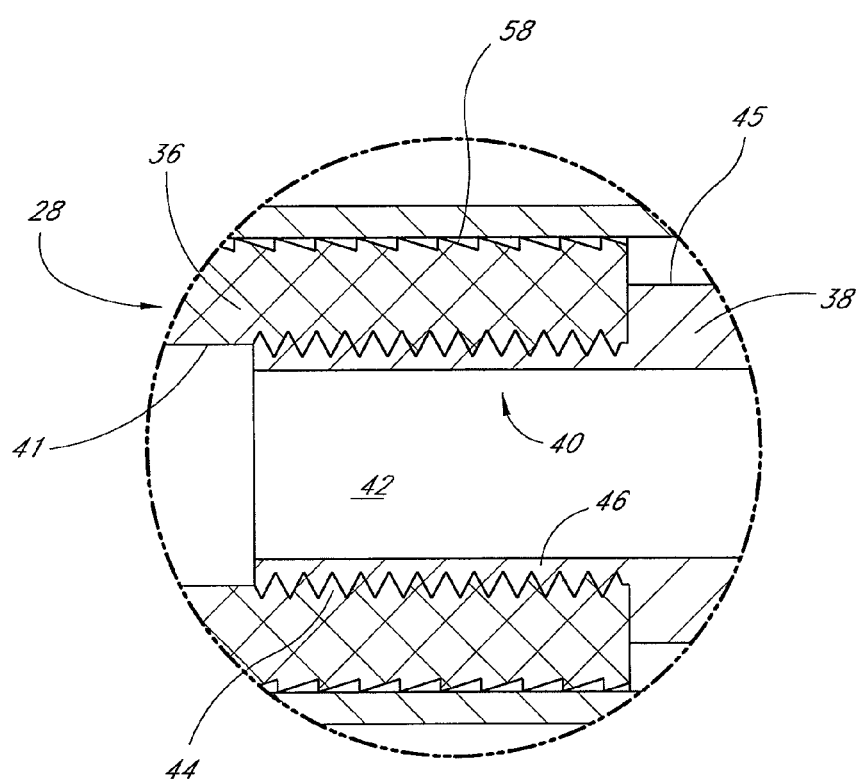
FIG. 4A is an enlarged view of portion 4A of FIG. 4.

With particular reference to FIGS. 3, 4, and 4A, the body 28 comprises a first portion 36 and a second portion 38 that are coupled together at a junction 40. In the illustrated embodiment, the first portion 36 carries the distal anchor 34 while the second portion 38 forms the proximal end 30 of the body 28. As will be explained in more detail below, in certain embodiments, the second portion 38 may be used to pull the body 28 and therefore will sometimes be referred to as a "pull-pin". The first and second portions 36, 38 are preferably detachably coupled to each other at the junction 40. In the illustrated embodiment, the first and second portions 36, 38 are detachably coupled to each other via interlocking threads. Specifically, as best seen in FIG. 4A, the body 28 includes an inner surface 41, which defines a central lumen 42 that preferably extends from the proximal end 30 to the distal end 32 throughout the body 28. At the proximal end of the first portion 36, the inner surface 41 includes a first threaded portion 44. The first threaded portion 44 is configured to mate with a second threaded portion 46, which is located on the outer surface 45 of the second portion 38. The interlocking annular threads of the first and second threaded portions 44, 46 allow the first and second portions 36, 38 to be detachably coupled to each other. In one modified embodiment, the orientation of the first and second threaded portions 44, 46 can be reversed. That is, the first threaded portion 44 can be located on the outer surface of the first portion 36 and the second threaded portion 46 can be located on the inner surface 41 at the distal end of the second portion 38. Any of a variety of other releasable complementary engagement structures may also be used, to allow removal of second portion 38 following implantation, as is discussed below.

In a modified arrangement, the second portion 38 can comprise any of a variety of tensioning elements for permitting proximal tension to be placed on the distal anchor 34 while the proximal anchor is advanced distally to compress the fracture. For example, any of a variety of tubes or wires can be removably attached to the first portion 36 and extend proximally to the proximal handpiece. In one such arrangement, the first portion 36 can include a releasable connector in the form of a latching element, such as an eye or hook. The second portion 38 can include a complementary releasable connector (e.g., a complementary hook) for engaging the first portion 36. In this manner, the second portion 38 can be detachably coupled to the first portion 36 such proximal traction can be applied to the first portion 36 through the second portion as will be explained below. Alternatively, the second portion 48 may be provided with an eye or hook, or transverse bar, around which or through which a suture or wire may be advanced, both ends of which are retained at the proximal end of the device. Following proximal tension on the tensioning element during the compression step, one end of the suture or wire is released, and the other end may be pulled free of the device. Alternate releasable proximal tensioning structures may be devised by those of skill in the art in view of the disclosure herein. It should also be appreciated that the body may be from a single piece as described in U.S. Pat. No. 6,511,481, which has been incorporated by reference herein.

As shown in FIG. 4, the body 28 is cannulated to accommodate installation over a placement wire as is understood in the art. The cross section of the illustrated central cannulation is circular but in other embodiments may be non circular, e.g., hexagonal, to accommodate a corresponding male tool for installation or removal of the second portion 38 of the body 28 as explained above. In other embodiments, the body 28 may partially or wholly solid.

With continued reference to FIGS. 2-4, the proximal end 30 of the body 28 may be provided with a rotational coupling 70, for allowing the second portion 38 of the body 28 to be rotationally coupled to a rotation device. The proximal end 30 of the body 28 may be desirably rotated to accomplish one or two discrete functions. In one application, the proximal end 30 is rotated to remove the second portion 38 of the body 28 following tensioning of the device to anchor an attachment to the bone. Rotation of the rotational coupling 70 may also be utilized to rotationally drive the distal anchor into the bone. Any of a variety of rotation devices may be utilized, such as electric drills or hand tools, which allow the clinician to manually rotate the proximal end 30 of the body. Thus, the rotational coupling 70 may have any of a variety of cross sectional configurations, such as one or more flats or splines.

In one embodiment, the rotational coupling 70 comprises a proximal projection of the body 28 having an axial recess with a polygonal cross section, such as a hexagonal cross section. The rotational coupling 70 is illustrated as a female component, machined or milled or attached to the proximal end 30 of the body 28. However, the rotational coupling may also be in the form of a male element, such as a hexagonal or other noncircular cross sectioned projection.

The proximal end 30 of the fixation device is provided with a proximal anchor 50. Proximal anchor 50 is axially distally moveable along the body 28, to permit compression of between the distal and proximal ends 32, 30 of the fixation device 12. As will be explained below, complimentary locking structures such as threads or ratchet like structures between the proximal anchor 50 and the body 28 resist proximal movement of the anchor 50 with respect to the body 28 under normal use conditions. The proximal anchor 50 preferably can be axially advanced along the body 28 with and/or without rotation as will be apparent from the disclosure herein.

Referring to FIG. 4, the proximal anchor 50 comprises a housing 52 such as a tubular body, for coaxial movement along the body 28. As will be explained in more detail below, in certain embodiments, the housing 50 may have diameter sized to fit through an opening formed in fixation bar or plate.

In a final position, the distal end of the housing 52 preferably extends distally past the junction 40 between the first portion 36 and the second portion 38. The housing 52 is provided with one or more surface structures 54 such as a radially inwardly projecting flange 56 (see FIGS. 4B and 4C), for cooperating with complementary surface structures 58 on the first portion 36 of the body 28. In the illustrated embodiment, the complimentary surface structures 58 comprise a series of annular ridges or grooves 60. The surface structures 54 and complementary surface structures 58 permit distal axial travel of the proximal anchor 50 with respect to the body 28, but resist proximal travel of the proximal anchor 50 with respect to the body 28.

Figure 4B:
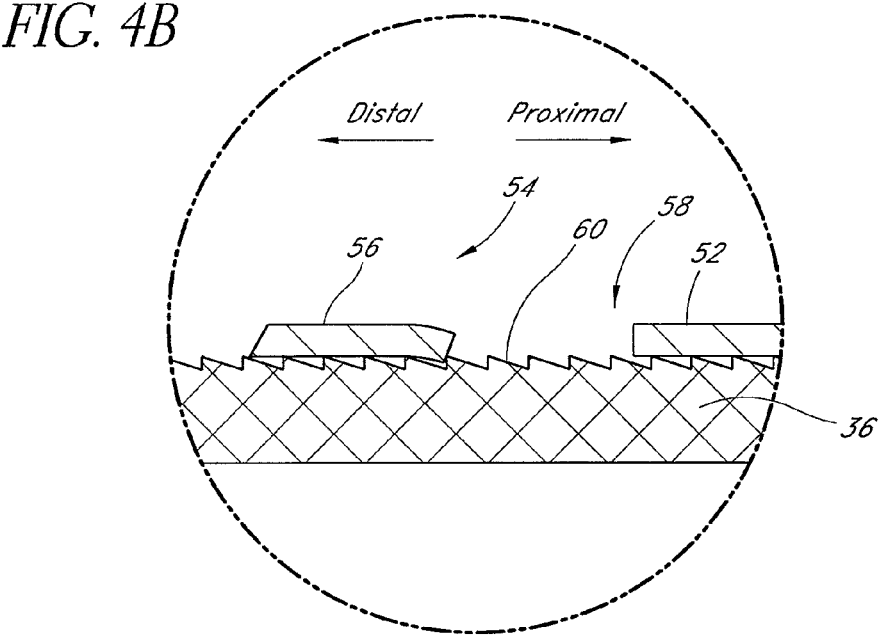
FIG. 4B is an enlarged view of portion 4B of FIG. 4 with the fixation device in a first position.
Figure 4C:
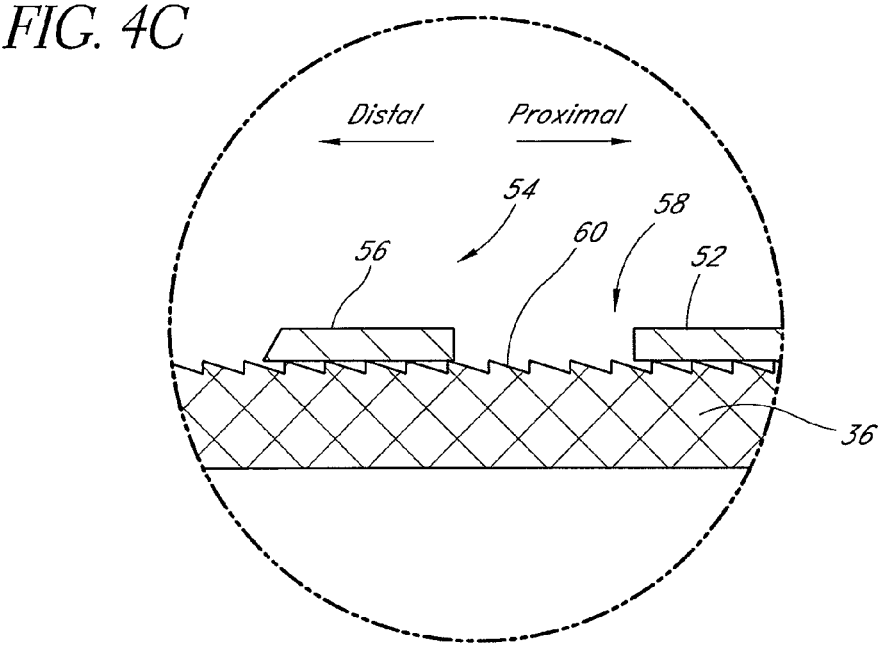
FIG. 4C is an enlarged view of portion 4C of FIG. 4 with the fixation device in a second position.

For example, as best seen in FIG. 4B, the proximal end of the flange 56 is biased towards the longitudinal axis of the body 28. As such, when the proximal anchor 50 is urged proximally with respect to the body 28, the flange 56 engages the grooves or ridges 60 of the complementary surface structures 58. This prevents proximal movement of the proximal anchor 50 with respect to the body 28. In contrast, as best seen in FIG. 4C, when the proximal anchor 50 is moved distally with respect to the body 28, the flange 56 can bend outwardly away from the body 28 and the ridges 60 so as to allow the proximal anchor 50 to move distally. Of course, those of skill in the art will recognize that there are a variety of other complementary surface structures, which permit one way ratchet like movement. For example, a plurality of annular rings or helical threads, ramped ratchet structures and the like for cooperating with an opposing ramped structure or pawl can also be used. In one embodiment, opposing screw threads are dimensioned to function as a ratchet.

Retention structures 58 are spaced axially apart along the body 28, between a proximal limit 62 and a distal limit 64. The axial distance between proximal limit 62 and distal limit 64 is related to the desired axial working range of the proximal anchor 50, and thus the range of functional sizes of the fixation device 12. Thus, the fixation device 12 of the exemplary embodiment can provide compression between the distal anchor 34 and the proximal anchor 50 vertebrae throughout a range of motion following the placement of the distal anchor in a vertebra. That is, the distal anchor may be positioned within the cancellous and/or distal cortical bone of a vertebra, and the proximal anchor may be distally advanced with respect to the distal anchor throughout a range to provide compression without needing to relocate the distal anchor and without needing to initially locate the distal anchor in a precise position with respect to the proximal side of the bone or another vertebra. Providing a working range throughout which tensioning of the proximal anchor is independent from setting the distal anchor allows a single device to be useful for a wide variety of spinal fixation procedures, as well as eliminates the need for accurate device measurement. In addition, this arrangement allows the clinician to adjust the compression force during the procedure without adjusting the position of the distal anchor. In this manner, the clinician may focus on positioning the distal anchor sufficiently within the vertebra to avoid or reduce the potential for distal migration out of the vertebra, which may damage the particularly delicate tissue, blood vessels, nerves and/or spinal cord surrounding or within the spinal column.

In many applications, the working range is at least about 10% of the overall length of the device, and may be as much as 20% or 50% or more of the overall device length. In the context of a spinal application, working ranges of up to about 10 mm or more may be provided, since estimates within that range can normally be readily accomplished within the clinical setting. The embodiments disclosed herein can be scaled to have a greater or a lesser working range, as will be apparent to those of skill in the art in view of the disclosure herein.

With reference back to FIGS. 2-4, the proximal anchor 50 includes a flange 66 that, as will be explained below, may be configured to sit against the outer surface of a vertebra and/or a fixation rod or plate. The flange 66 is preferably an annular flange, to optimize the footprint or contact surface area between the flange 66 and the bone or fixation rod or plate. Circular or polygonal shaped flanges for use in spinal fixation will generally have a diameter of at least about 3 mm greater than the adjacent body 28 and often within the range of from about 2 mm to about 30 mm or more greater than the adjacent body 28.

Figure 5:
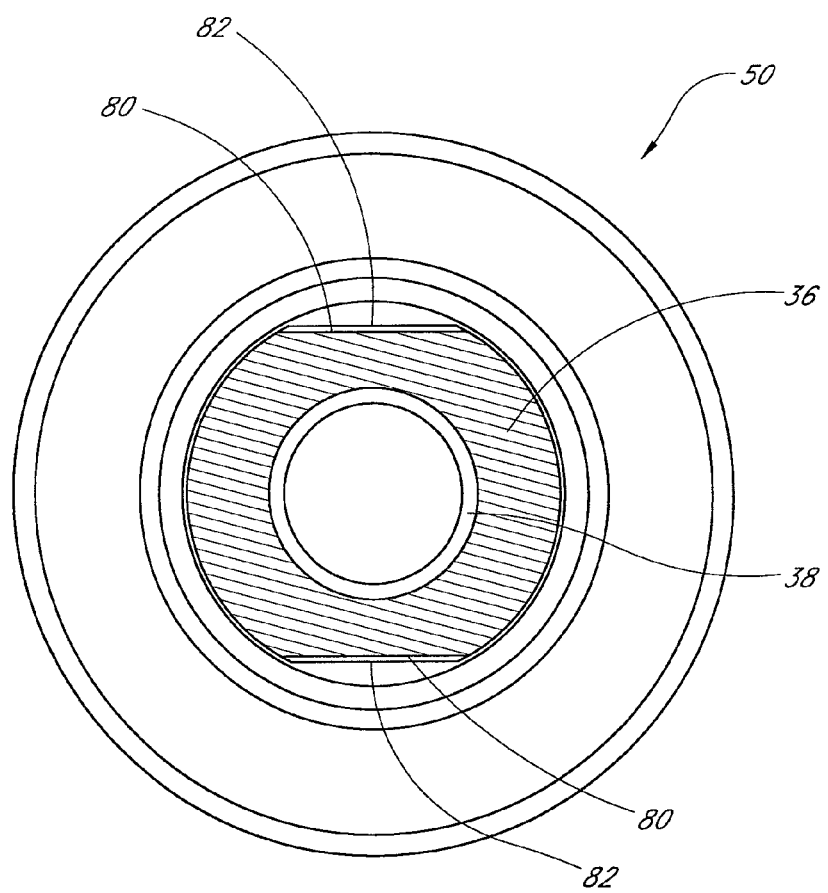
FIG. 5 is a cross-sectional view taken through line 5-5 of FIG. 3.

With particular reference to FIGS. 2 and 5, the fixation device may include an antirotation lock between the first portion 36 of the body 28 and the proximal collar 50. In the illustrated embodiment, the first portion 36 includes a pair of flat sides 80, which interact with corresponding flat structures 82 in the proximal collar 50. One or three or more axially extending flats may also be used. As such, rotation of the proximal collar 50 is transmitted to the first portion 36 and distal anchor 34 of the body 28. Of course, those of skill in the art will recognize various other types of splines or other interfit structures can be used to prevent relative rotation of the proximal anchor and the first portion 36 of the body 28.

To rotate the proximal collar, the flange 66 is preferably provided with a gripping structure to permit an insertion tool to rotate the flange 66. Any of a variety of gripping structures may be provided, such as one or more slots, flats, bores or the like. In one embodiment, the flange 44 is provided with a polygonal, and, in particular, a pentagonal or hexagonal recess 84 (see FIG. 4).

In a modified embodiment, the housing 52 of the proximal anchor 50 can include one or more one or more barbs that extend radially outwardly from the tubular housing 52. Such barbs provide for self tightening after the device has been implanted in the patient as described in a co-pending U.S. patent application Ser. No. 10/012,687, filed Nov. 13, 2001, which was incorporated by reference above. The barbs may be radially symmetrically distributed about the longitudinal axis of the housing 52. Each barb is provided with a transverse engagement surface, for anchoring the proximal anchor 50 in the bone. The transverse engagement surface may lie on a plane which is transverse to the longitudinal axis of the housing 50 or may be inclined with respect to the longitudinal axis of the tubular 50. In either arrangement, the transverse engagement surface 43 generally faces the contacting surface 68 of the flange 44. As such, the transverse engagement surface inhibits proximal movement of the proximal anchor with respect to the bone.

Figure 6A:
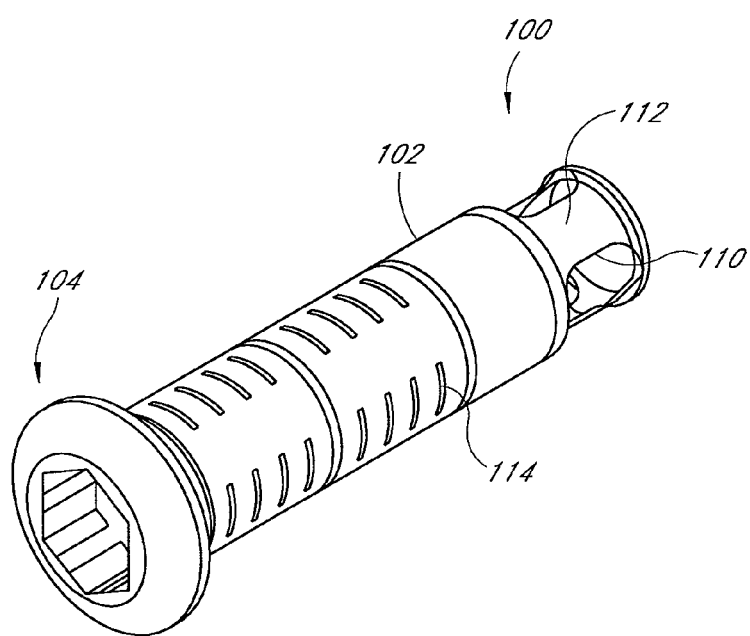
FIG. 6A is a side perspective view of another embodiment of a proximal anchor for the bone fixation device of FIG. 1.
Figure 6B:
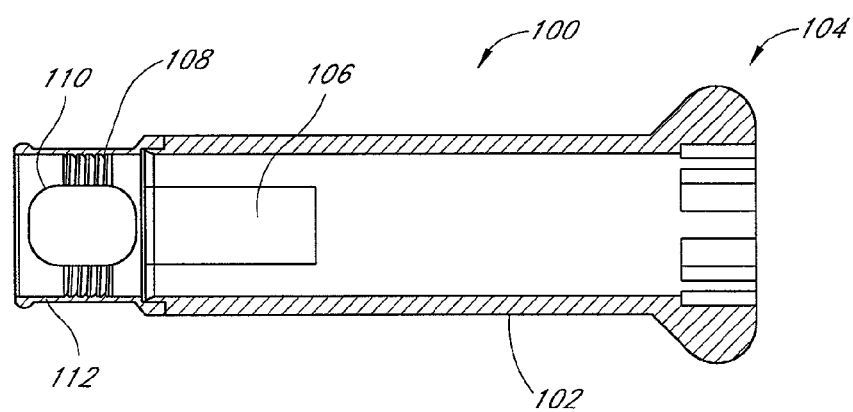
FIG. 6B is a cross-sectional view of the proximal anchor of FIG. 6A.

FIGS. 6A and 6B illustrate another embodiment of a proximal anchor 100. This embodiment also includes a tubular housing 102 and a flange 104 that may be configured as describe above with respect to FIGS. 2-4. The tubular housing 102 may include an anti-rotational lock, which, in the illustrated embodiment, is in the form of one or more sides 106 that interact with corresponding flat structures formed in the body 28 as described above.

In this embodiment, the surfaces structures comprises one or more teeth or grooves 112, which are configured to engage the complementary surfaces structures on the body 28 (see FIG. 2). One or more slots or openings 110 are formed in the tubular housing 102 to form one or more bridges 112, which carry the teeth 102. The anchor proximal anchor 100 may be pushed towards the distal end of the body and the teeth 102 can slide along the and over the complementary surface structures 58 on the body 28. In the illustrated embodiment, the bridge 113 may flex slightly away from the body 28 to allow such movement. The number and shape of the openings 110 and bridges 112 may be varied depending of the desired flexing of the bridges 112 when the proximal anchor 110 is moved distally over the body and the desired retention force of the distal anchor when appropriately tensioned. In one embodiment, the teeth on the proximal anchor 100 and the grooves on the body 28 may be configured such that the proximal anchor 100 can be rotated or threaded onto the pin in the distal direct and/or so that that the proximal anchor can be removed by rotation. The illustrated embodiment also advantageously includes visual indicia 114 (e.g., marks, grooves, ridges etc.) on the tubular housing 102 for indicating the depth of the proximal housing 100 within the bone.

Figure 6C:
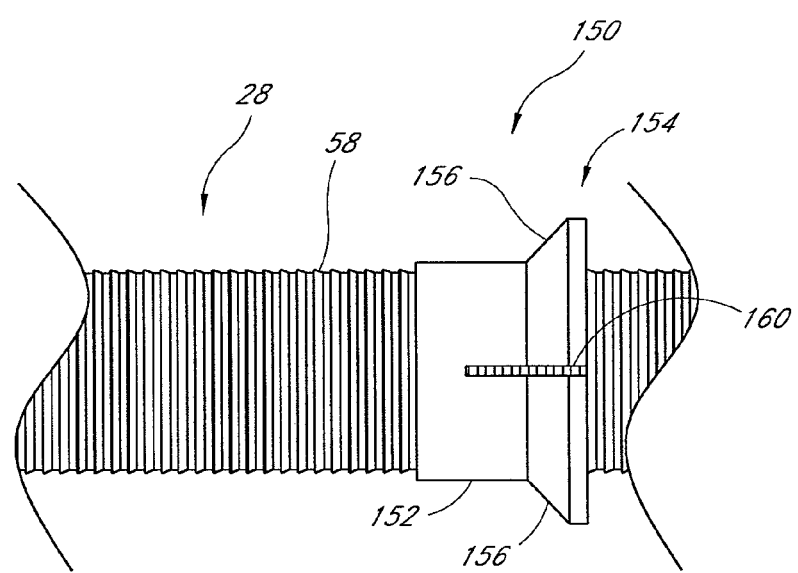
FIG. 6C is a side perspective view of another embodiment of a proximal anchor for the bone fixation device of FIG. 1.
Figure 6D:
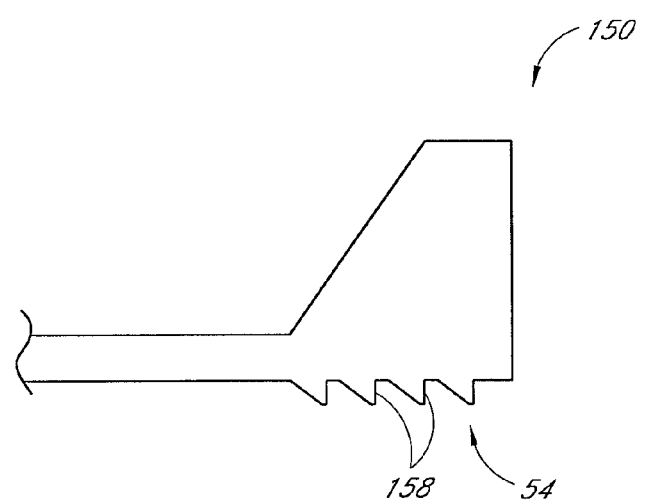
FIG. 6D is a cross-sectional view of the proximal anchor of FIG. 6C.

FIGS. 6C and 6D illustrate another embodiment of a proximal anchor 150. In this embodiment, the proximal anchor 150 comprises a housing 152 such as a tubular body, for coaxial movement along the body 28. The proximal anchor 150 also includes a flange 154 that is configured that to set against the outer surface of, for example, a bone or fixation bar or rod. In the illustrated embodiment, the flange 154 defines a contacting surface 156, which preferably forms an obtuse angle with respect to the exterior of the housing 152. However, in modified embodiments, the contacting surface 154 may be perpendicular or form an acute angle with respect to the housing 152.

Referring to FIG. 6D, in the illustrated embodiment, the complementary retention structures 54 comprise one or more inwardly projecting teeth or flanges 158, for cooperating with the complementary rentention structures 58 on the body 28. The complementary retention structures 58 of the body preferably comprise a plurality of annular ridges or grooves a first surface and a second surface. The first surface generally faces the proximal direction and is preferably inclined with respect to the longitudinal axis of the body 28. In contrast, the second surface generally faces the distal direction and lies generally perpendicular to the longitudinal axis of the body 28.

The proximal anchor 150 preferably includes one or more of axial slots 160. The axial slots 160 cooperate to form lever arm(s) on which the teeth or projections 158 are positioned.

Thus, as the anchor 150 is pushed towards the distal end of the body 28, the teeth 158 can slide along the first surface and ride over the retention structures 58 of the body 28 as the teeth 158 are flexed away from the body 28.

After appropriate tensioning of the proximal anchor 150, the bone may push on the angled portion contacting surface 156 of the proximal anchor 150. This force is transmitted to the teeth 158 through the lever arms. As such, the teeth 158 are prevented from flexing away from the body 28, which keeps the teeth 158 engaged with the retention structures 58 of the body 28. By increasing the tensioning force, proximal movement of the proximal anchor 150 with respect to the body 28 is resisted.

The axial length and width of the slots 160 may be varied, depending upon the desired flexing of the lever arms when the proximal anchor 150 is moved distally over the body 28 and the desired retention force of the distal anchor when appropriately tensioned. For a relatively rigid material such as titanium, axial lengths and widths of the slots 160 are approximately 0.5 mm for a proximal anchor having a length of approximately 4 mm, an inner diameter of approximately 3 mm. As such, in the illustrated embodiment, the slots 160 extend through the flange 154 and at least partially into the housing 152.

In this embodiment, the proximal anchor 150 includes four teeth or flanges 158, which are positioned near the proximal end of the anchor 150. In modified embodiments, the proximal anchor 150 may include more or lest teeth and/or the teeth may be positioned and/or distally or proximally on the anchor 150. It should also be appreciated that these retention structures may be configured such that the proximal anchor 150 may be proximally and/or distally advanced with rotation by providing for a screw like configuration between the retention structures.

Figure 6E:
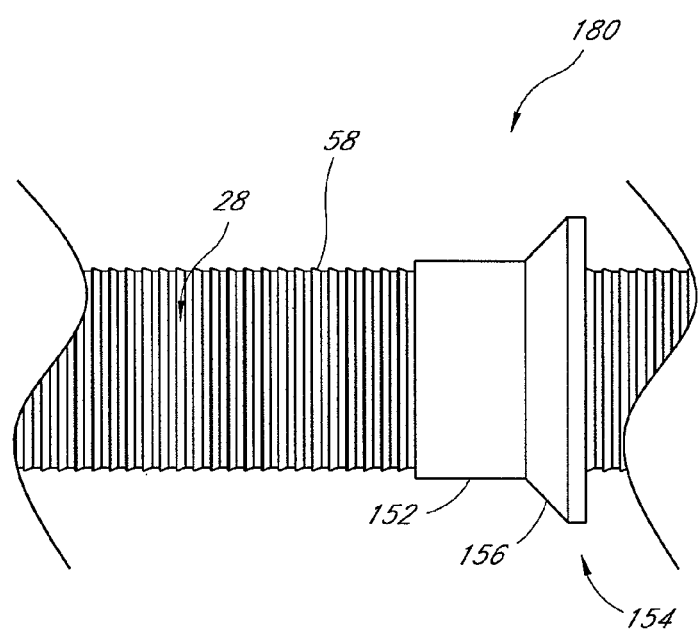
FIG. 6E is a cross-sectional view of another embodiment of a proximal anchor for the bone fixation device of FIG. 1.
Figure 6F:
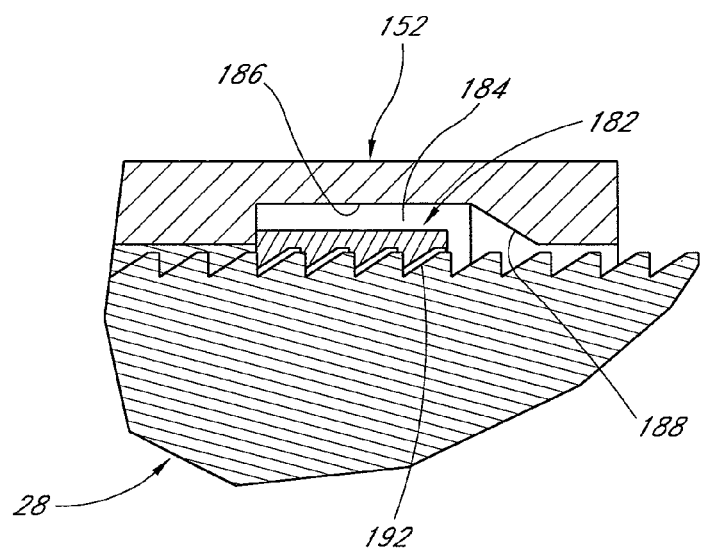
FIG. 6F is a cross-sectional view of the proximal anchor of FIG. 6E.

Another embodiment of a proximal anchor 180 is illustrated in FIGS. 6E and 6F. As with the previous embodiment, the proximal anchor 180 may include a tubular housing 152 and a flange 154 with a bone contacting surface 156. In this embodiment, the complementary structure of the proximal anchor 180 comprises an annular ring 182, which is positioned within an annular recess 184 that is preferably positioned at the distal end of the tubular housing 152. The annular recess 184 includes a proximal portion 186 and a distal portion 188.

The proximal portion 186 is sized and dimensioned such that as the proximal anchor 180 is advanced distally over the body 28 the annular ring 182 can ride over the complementary retention structures 58 of the body 28. That is, the proximal portion 182 provides a space for the annular ring 182 can move radially away from the body 28 as the proximal anchor 180 is advanced distally. Preferably, the annular ring 182 is made from a material that provides sufficient strength and elasticity such as, for example, stainless steel or titanium. The annular ring 182 is preferably split such that it can be positioned over the body 405. In the illustrated embodiment, the annular ring 182 includes a plurality of teeth 192 although in modified embodiments the annular ring 182 may be formed without the teeth.

The distal portion 188 of the recess 184 is sized and dimensioned such that after the proximal anchor 180 is appropriately tensioned the annular ring 192 becomes wedged between the body 28 and an angled engagement surface of the distal portion 188. In this manner, proximal movement of the proximal anchor 180 with respect to the body is prevented. Although not illustrated, it should be appreciated that in modified embodiments, the ring 192 can be formed without a gap. Other embodiments and further details of the proximal anchor described above can be found in U.S. patent application Ser. No. 09/990,587, filed Nov. 19, 2001, which is hereby incorporated by reference herein.

With reference back to FIGS. 2-4, in the illustrated embodiment, the contacting surface 68 of the flange 44 is tapered and generally faces the outer surface of the vertebra, fixation rod, and/or plate. In other embodiments, the bone contacting surface 69 can reside in or approximately on a plane, which is perpendicular with respect to the longitudinal axis of the body 28. In other embodiments, other angular relationships between the bone contacting surface 68 of the flange 66 and the longitudinal axis of the body 28 and housing 52 may be utilized, depending upon the anticipated entrance angle of the body 28 and associated entrance point surface of the vertebra.

The clinician may be provided an array of proximal anchors 50 of varying angular relationships between the contacting surface 68 and the longitudinal axis of the body 28 and housing 52 (e.g., 90°, 100°, 110°, 120°, and 130°). A single body 28 can be associated with the array such as in a single sterile package. The clinician upon identifying the entrance angle of the body 28 and the associated entrance point surface orientation of the facet joint of the spine can choose the anchor 50 from the array with the best fit angular relationship, for use with the body 28.

Figure 8:
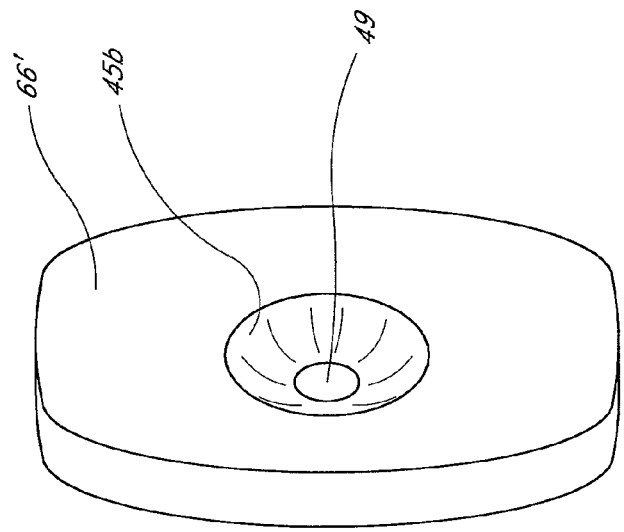
FIG. 8 is a front perspective view of the proximal anchor plate of FIG. 7.
Figure 7:
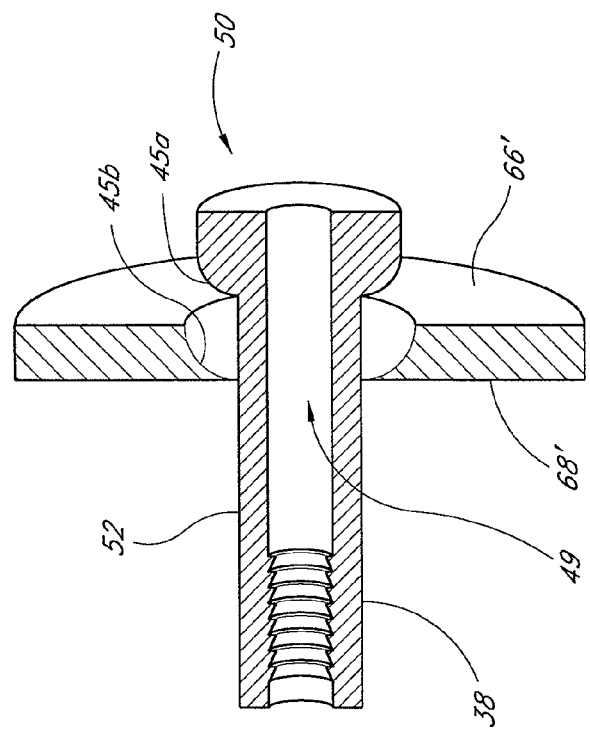
FIG. 7 is a cross sectional view through an angularly adjustable proximal anchor plate.
Figures 9, 10, 11:
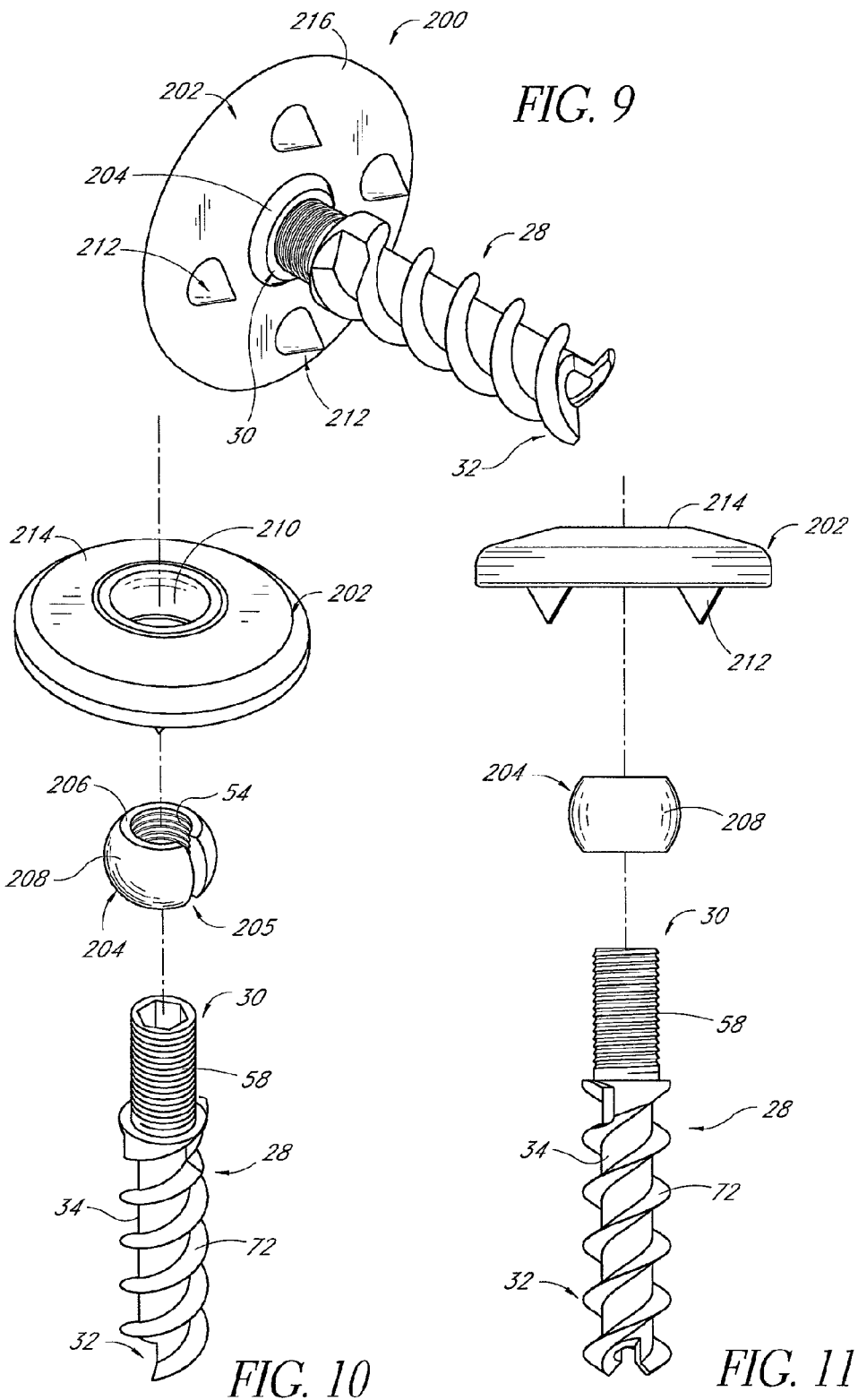
FIG. 9 is a bottom perspective view of a modified embodiment of a bone fixation device.
FIG. 10 is an unassembled side perspective view of the bone fixation device of FIG. 9.
FIG. 11 is an unassembled side view of the bone fixation device of FIG. 9.

In accordance with a modified arrangement, illustrated in FIGS. 7 and 8, the proximal anchor 50 may be used with a washer 66' that is angularly adjustable with respect to the longitudinal axis of the body 28. More specifically, in this embodiment, the proximal anchor 50 and the washer 66' include corresponding semi-spherical or radiused surfaces 45a and 45b. The surface 45b surrounds an aperture 49 in the washer 66. This arrangement allows the proximal anchor 50 to extend through and pivot with respect to the washer 66'. As such, the angular relationship between the bone contacting surface 68' of the washer 66' and the longitudinal axis of the body 28 can vary in response to the entrance angle.

FIGS. 9-13 illustrate another embodiment of a bone fixation device 200 with an angularly adjustable proximal anchor 202. In this embodiment, similar reference numbers are used to identify components that are similar components described above.

The bone fixation device 200 comprises a body 28 that extending between a proximal end 30 and a distal end 32. The distal end 32 of the body is provide with a bone anchor 34 as described above. The illustrated body 28 is cannulated; however, it should be appreciated that in modified embodiments the body 28 can be solid. The proximal end of the anchor is provided with a hexagonal recess, which can be used in combination with a rotational tool to rotate the body 28. Of course, modified embodiments may use a variety of different male or female anti-rotational couplings.

The illustrated fixation device includes an annular flange 202 and proximal anchor 204. As with the proximal anchor described above, the proximal anchor 204 defines a housing 206 that is axially distally moveable along the body 28. Complimentary locking structures 54, 58 on the housing 206 and the body 28 such as threads or ratchet like structures resist proximal movement of the anchor 204 with respect to the body 28 under normal use conditions. In some embodiments, the complimentary locking structures 54, 48 may permit the anchor 204 to be axially advanced along the body 28 by rotation. In other embodiments, the complimentary locking structures 54, 58 may permit the anchor 204 to be axially advanced along the body 24 without rotation. The illustrated proximal anchor 204 also includes a gap 205 such that the illustrated anchor 204 forms a split ring collar. In modified embodiments, the proximal anchor 204 can be formed without the gap 205.

The proximal anchor 204 preferably includes a smooth and more preferably rounded or spherical outer surface portion 208, which is configured to fit within a corresponding smooth and preferably rounded recessed portion 210 in the flange 202. As such, as shown in FIG. 12, when the proximal anchor 204 is positioned in the flange 202, the flange 202 resists distal movement of the proximal anchor 204 while permitting at least limited rotation of between the proximal anchor 204 and the flange 202. As such, the illustrate arrangement allows for angular movement of the flange 202 with respect to the anchor 204 to accommodate variable anatomical angles of the bone surface. As will be explained in more detail below, this embodiment is particularly advantageous for trans-laminar, trans-facet and facet-pedicle applications. In such applications, the flange 202 may seat directly against the outer surface of a vertebra. Because the outer surface of the vertebra is typically non-planar and/or the angle of insertion is not perpendicular to the outer surface of the vertebra, a fixed flange may contact only a portion of the outer surface of the vertebra. This may cause the vertebra to crack due to high stress concentrations. In contrast, the angularly adjustable flange 202 can rotate with respect to the body and thereby the bone contacting surface may be positioned more closely to the outer surface. More bone contacting surface is thereby utilized and the stress is spread out over a larger area. In addition, the flange 202, which has a larger diameter than the proximal anchor 50, effectively increases the shaft to head diameter of the fixation device, thereby increasing the size of the loading surface and reducing stress concentrations.

In the illustrated embodiment, the flange 202 includes a plurality of bone engagement features 212, which in the illustrated embodiment comprises a one or more spikes 212 positioned on a contacting surface 216 of the flange 202. The spikes 212 provide additional gripping support especially when the flange 202 is positioned against, for example, uneven bone surfaces and/or soft tissue. However, it should be appreciated that in modified embodiments the flange 202 may be formed without the bone engagement features 212. Other structures for the bone engagement feature 212 may also be used, such as, for example, ridges, serrations etc. The illustrated embodiment also includes a tapered upper surface 214 that in certain embodiments may be flat.

Figure 14:
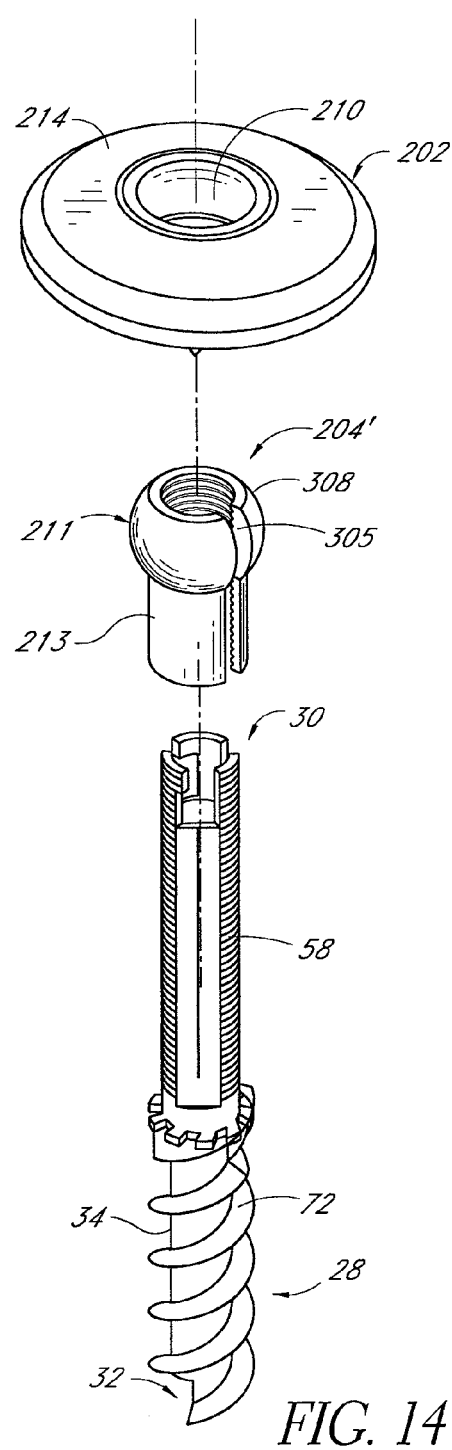
FIG. 14 is an unassembled side perspective view of another modified embodiment of a bone fixation device.
Figure 15:
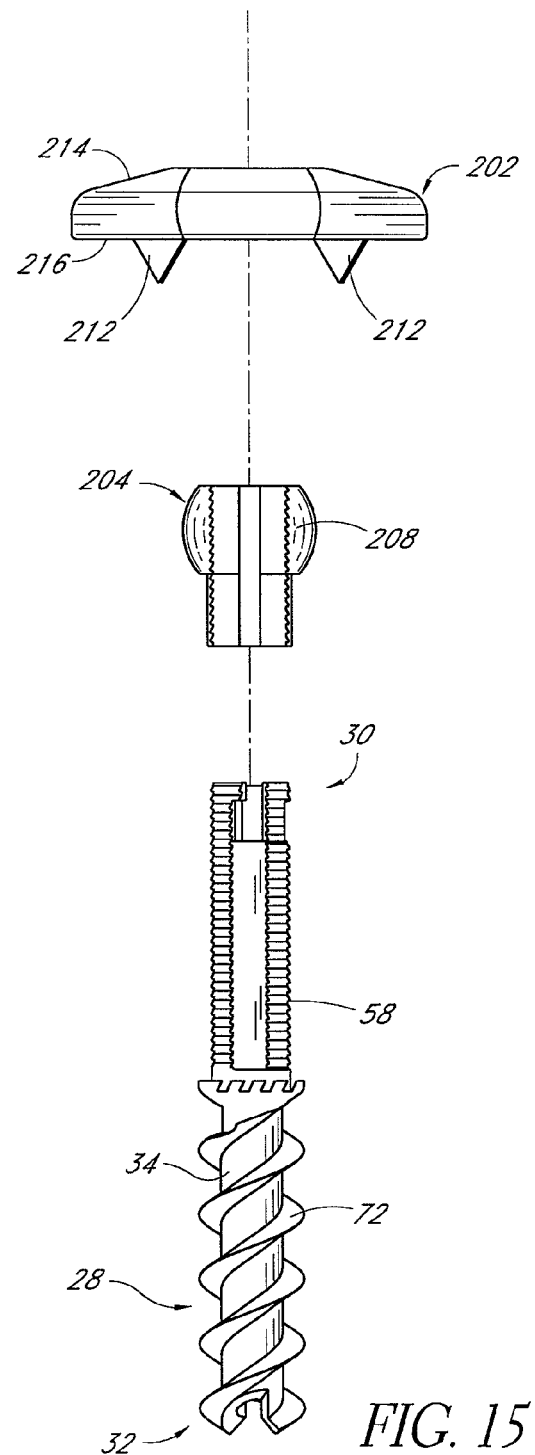
FIG. 15 is an unassembled side view of the bone fixation device of FIG. 9.

FIGS. 14 and 15 illustrate a modified embodiment of the angularity adjustable fixation device 200. In this embodiment, the proximal anchor 204' includes an upper portion 211 and a lower portion 213. The upper portion 211 is configured as described above with respect to the housing. The lower portion in the illustrated embodiment is generally tubular and a generally smaller diameter than the upper portion. The lower portion includes complementary retention structures 54 and generally provides the fixation device with a greater range of adjustable compression and additional retention structures as compared to the previous embodiment.

In one embodiment of use, a patient with a spinal instability is identified. Depending upon the spinal fixation technique, the distal ends 32 of one or more bone fixation devices described herein are advanced into the anterior vertebral body or other suitable portion of one or more vertebrae. As will be explained in more detail below, the fixation device is typically used to couple one vertebra that is unstable, separated or displaced to another vertebra, which is not unstable, separated or displaced. However, it should be appreciated that this method may also be applied to three or more vertebrae. In addition, the S-1 portion of the sacrum may be used to stabilize the L5 vertebrae.

For example, the fixation devices may be inserted into the vertebrae with bilateral symmetry such that such two vertebrae are coupled together with two or more fixation devices on a left side of the spine being connected using one or more rods and/or plates to two or more fixation devices on a right side of the spine. In certain of these embodiments, the distal anchor of these fixation devices may be inserted through the pedicle and/or the facet of the vertebrae. In other embodiments, the fixation devices will be utilized to secure adjacent vertebral bodies in combination with another fusion procedure or implant, such as the implantation of a spinal cage, plate or other device for fusing adjacent vertebral bodies. Thus, the fixation devices may operate in conjunction with a cage or other implant to provide three point stability across a disc space, to assist in resisting mobility between two vertebral bodies. In other embodiments, the fixation device may simply be advanced through a portion of a first vertebra and into a second, preferably adjacent, vertebra. In certain of these embodiments, the fixation device may extend through the facet of the first vertebra and the distal anchor may be inserted through the facet or pedicle of the second vertebra.

The proximal anchor may be carried by the fixation device prior to advancing the body into the vertebrae, or may be attached following placement of the body within the vertebrae. In one embodiment, stabilization implants (e.g., a fixation plate and/or rod) may be placed over or coupled to the body or the proximal anchor before the proximal anchor is placed on the body.

Once the anchor is in the desired location, proximal traction is applied to the proximal end 30 of body 28, such as by conventional hemostats, pliers or a calibrated loading device, while distal force is applied to the proximal anchor. In this manner, the proximal anchor is advanced distally with respect to the body until the proximal anchor fits snugly against the outer surface of the vertebra or a fixation plate/rod. Appropriate tensioning of the fixation device is accomplished by tactile feedback or through the use of a calibration device for applying a predetermined load on the implantation device. As explained above, one advantage of the structure of the illustrated embodiments is the ability to adjust compression independently of the setting of the distal anchor 34 within the vertebra.

Following appropriate tensioning of the proximal anchor, the second portion 38 of the body 28 is preferably detached from the first portion 36 and removed. In the illustrated embodiment, this involves rotating the second portion 38 with respect to the first portion via the coupling 70. In other embodiment, this may involve cutting the proximal end of the body 28. For example, the proximal end of the body may be separated by cauterizing. Cauterizing may fuse the proximal anchor 50 to the body 32 thereby adding to the retention force between the proximal anchor 50 and the body 28. Such fusion between the proximal anchor and the body may be particularly advantageous if the pin and the proximal anchor are made from a bioabsorbable and/or biodegradable material. In this manner, as the material of the proximal anchor and/or the pin is absorbed or degrades, the fusion caused by the cauterizing continues to provide retention force between the proximal anchor and the body.

Following or before removal of the second portion 38 of each body 28, additional fixations devices may be implanted and/or additional stabilization implants (e.g., rods, plates, etc.) may be coupled to the body. The access site may be closed and dressed in accordance with conventional wound closure techniques.

In a modified arrangement, the second portion 38 may form part of the driving device, which is used to rotate the proximal anchor 50 and thus cancellous bone anchor 34 into the vertebrae. The second portion 38 is used to apply proximal traction. After appropriate tensioning, the second portion 38 can be de-coupled from the first portion 36 and removed with the driving device.

In the foregoing variation, the second portion 38 may be connected to a rotatable control such as a thumb wheel on the deployment device. A container may be opened at the clinical site exposing the proximal end of the implant, such that the distal end of the second portion 38 may be removably coupled thereto. Proximal retraction of the hand tool will pull the implant out of its packaging. The implant may then be positioned within the aperture in the bone, rotated to set the distal anchor, and the hand piece may be manipulated to place proximal traction on the second portion 38 while simultaneously distally advancing the proximal anchor. Following appropriate tensioning, the second portion 38 may be disengaged from the implant, and removed from the patient. In the example of a threaded engagement, the second portion 38 may be disengaged from the implant by rotating a thumb wheel or other rotational control on the hand piece. In an alternate embodiment, such as where the second portion 38 comprises a pull wire, following appropriate tensioning across the fracture, a first end of the pull wire is released such that the pull wire may be removed from the implant by proximal retraction of the second end which may be attached to the hand piece.

Preferably, the clinician will have access to an array of fixation devices 12, having, for example, different diameters, axial lengths and, if applicable, angular relationships. These may be packaged one or more per package in sterile or non-sterile envelopes or peelable pouches, or in dispensing cartridges which may each hold a plurality of devices 12. The clinician will assess the dimensions and load requirements, and select a fixation device from the array, which meets the desired specifications.

Figure 16:
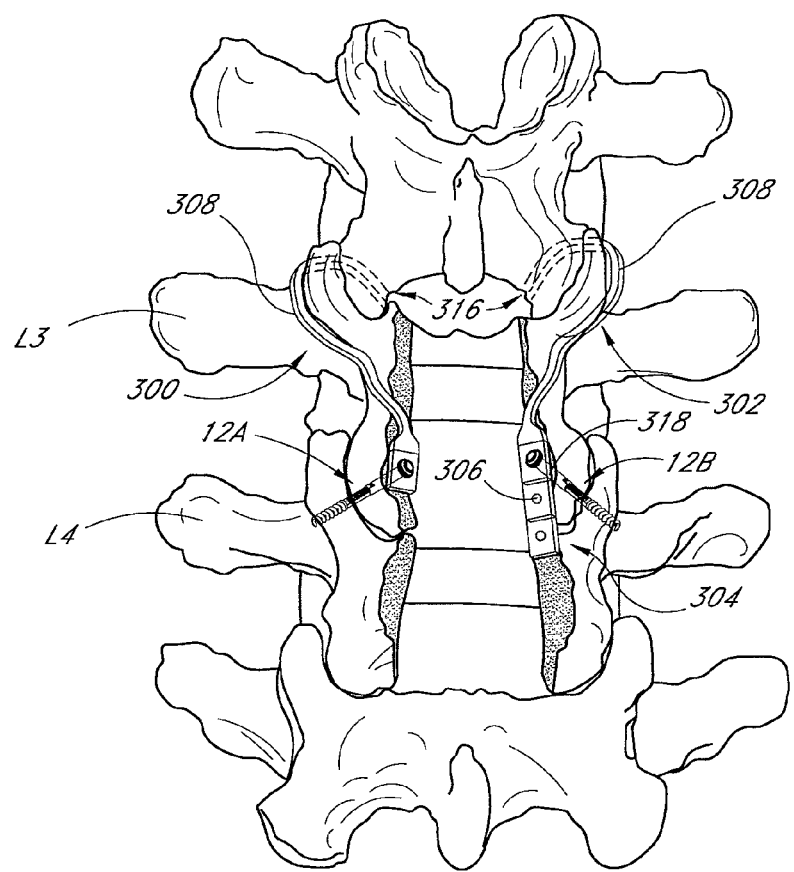
FIG. 16 is a posterior view of a portion of the spinal column and a fixation system including the fixation device of FIG. 1.

As mentioned above, the fixation device 12 of may be used with a variety spinal cages, plates or other devices for fusing adjacent vertebral bodies. For example, FIG. 16 illustrates a pair of fixation devices screws 12A, 12B according to the exemplary embodiments being used with a pair of fixation bars 300, 302 for spinal fixation. In this embodiment, the fixation devices 12A, 12B and the fixation bars 300, 302 are illustrated as fixing the L3 and L4 vertebrae relative to each other; however, theses components can be used to fix other adjacent or non-adjacent vertebrae in the lumbar region, as well as the thoracolumbar junction, or elsewhere on the spine as long as an axial path between two vertebra to compress the two vertebrae.

Figure 17:
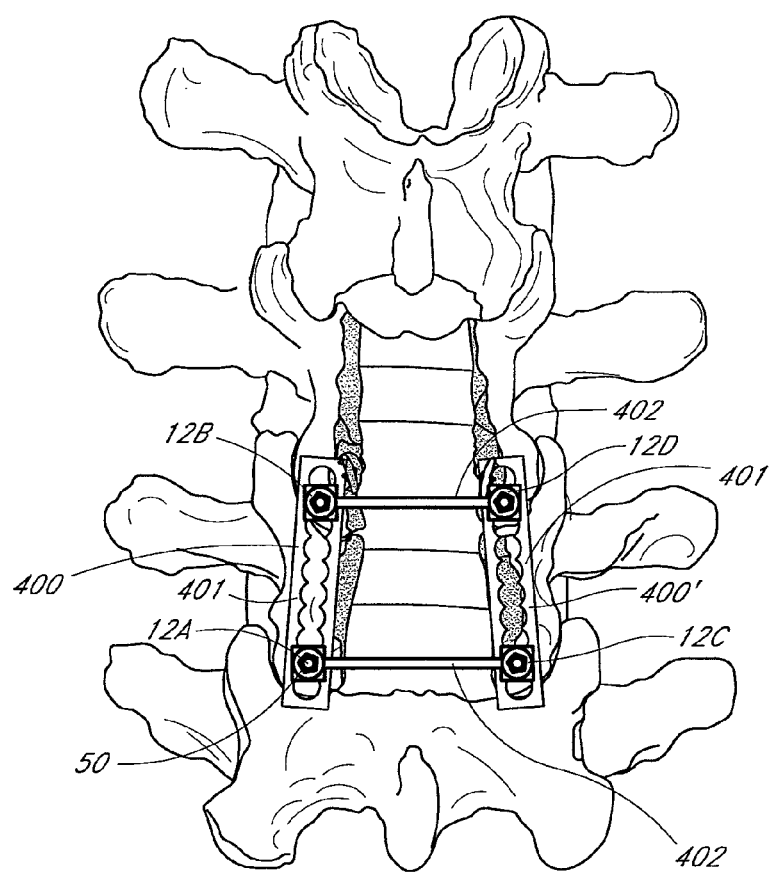
FIG. 17 is a posterior view of the spinal column and a modified fixation system that includes the fixation device of FIG. 1.

As shown in FIGS. 16 and 17, a laminectomy has been performed on the L3 and L4 vertebrae. Thus, the spinous process and the underlying lamina on each side of the sagittal plane have been removed, leaving only the outlying portion of the lamina transverse of the sagittal plane on both the L3 and L4 vertebrae. In one embodiment, the first fixation device 12A is inserted through the lamina of the L3 vertebra in the region of the facet joint on the left side of the sagittal plane. The first fixation device 12A will extend in an anterior direction through the facet joint and angles laterally outwardly into the left base of the transverse process of the inferior vertebra L4. A second fixation device 12B extends in an anterior direction through the lamina on the opposite (right) side of the sagittal plane. The second fixation device 12B extends through the facet joint on the right side of the sagittal plane and angles laterally outwardly into the right base of the transverse process of the L4 vertebra. Thus, the fixation devices 12A, 12B diverge in the anterior direction, and are also angled slightly in the inferior direction.

Each of the fixation devices 12A, 12B may be fitted within a fixation bar 300, 302. It should be appreciated that the fixation bar 300, 302 of FIG. 15 is merely exemplary and the fixation device may be used with other types and styles of fixation bars.

In the illustrated embodiment, the fixation bars 300 and 302 are generally mirror images of each other. The exemplary fixation bars 300, 302 includes an inferior portion 304 having a plurality of cylindrical bores 306. Each of the bores 306 are generally oriented along parallel axes and spaced in an inferior-superior direction along the inferior bar portion 304. The fixation devices 12A, 12B extend through one of the bores 306. By choosing the appropriate bore 306 for the fixation bar 300, 304, the relative length of the bar 300, 302 can be varied to provide adjustability for different sized vertebra. Each bar 300, 302 has a finger 308 that extends in a superior, and slightly lateral, direction from the inferior portion 306. The finger 308 extends in a superior direction across the cephalad side of the lateral process of L3 and curves in a superior and anterior direction over the superior aspect of the lateral pedicle of L3. The finger 308 then extends in an inferior direction and slightly laterally inwardly before terminating in an anterior end 316 short of the spinal cavity 50. The superior portion of the finger 308 thus forms a hook that extends over and around the L3 pedicle to secure the bar from movement in an inferior direction as well as to prevent rotational movement about the longitudinal axis of the bar.

The body 28 of the fixation device can be inserted through the bore 306. The housing 52 of the proximal anchor 50 is also dimensioned such that it has a diameter that is slightly less than the diameter of the bores 42 so as to allow rotational and reciprocal movement of the fixation device 12A, 12B in the bore 306, but not to allow the fixation device 12A, 12B toggle relative to its longitudinal axis. The flange 66 of the proximal anchor 50 has a diameter that is larger than the bore 42. Thus, the combination of the finger 44 wrapped around the superior portion of the lateral process 46 and the coaction of the fixation device 12A holding inferior portion 304 in place will prevent the toggling of the fixation device 12A, 12B relative to the lamina on the superior vertebra.

The inferior portion 304 of the bar 300, 302 may also carry a plurality of lateral weakened zones 318 in the form of lateral notches on both surfaces of the inferior portion 304 between each of the bores 306. With the manipulation of the proper tool, one or more sections containing bores 306 can be broken away from the stabilization bar to adjust the length of the inferior portion 304, so that unnecessary portions of the inferior portion can be removed. In FIG. 16, the left stabilization bar 300 is shown with the lower two segments of the inferior portion removed. In addition, the second portion 38 of the body 28 (see FIG. 4) are also illustrated as being removed after the stabilization bars 300 and 302.

Proximal retraction of the body 28 with respect to the proximal anchor 50 will compress the inferior portion 304 against the vertebra and will hold the stabilization bars 300, 302 rigidly and prevent toggling of the screws. One advantage of the illustrated embodiment is that compression of the inferior portion 304 against the vertebra may be adjusted independently of the setting of the distal anchor in the spine.

FIG. 17 illustrates a modified embodiment of a spinal fixation system. In this embodiment, four fixation devices 12A, 12B, 12C, 12D, are positioned in the facets of adjacent vertebra on both the left and right side of the vertebra column. A first set of the fixation devices 12A, 12B are used to secure opposing ends of a first fixation plate 400 to the facets of adjacent vertebrae and a second set of fixation devices 12C, 12D are be used to secure opposing ends of a second fixation plate 400' to the opposing facets on the adjacent vertebra. The fixation plates 400, 400' may include a series of overlapping bores 401 through which the body of the fixation device 12A, 12B may extend. The proximal anchor 50 may then be inserted over the body (not shown) and proximal retraction may be used to secure the fixation plate 400 against the vertebra.

The fixation hardware may also include cross-links 402, which span across the midline between corresponding fixation devices 12A, 12B, 12C, 12D on opposite sides of the spine. The cross-links 402 also includes bores through which the body and the tubular portion of the housing 50 extends. In modified embodiments, the fixation hardware may not include the cross-links 402.

Although not illustrated, it should be appreciated that the fixation devices described herein may be used as pedicle screws to secure a fixation rod or plate that extends between two or more vertebrae. Such applications may be used unilaterally or with bilateral symmetry.

In the embodiments of FIGS. 16 and 17, the use of the fixation device 12 advantageously allows the compression of the plates or fixation bars against the vertebrae to be adjusted independently of the setting of the distal anchor 34. That is, the proximal anchor 50 is advanced distally with respect to the body 28 until the proper compression load is applied across the fixation bars/plates and the vertebrae.

In a modified embodiment, the proximal anchor can be coupled to or form a part of the plate or fixation bar. Such an arrangement provides for self tightening after the device has been implanted into the patient.

Figure 18:
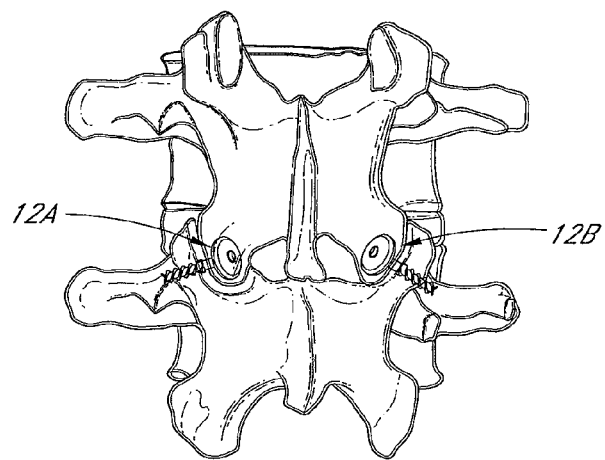
FIG. 18 is a posterior view of a portion of the lumbar spine with the fixation device of FIG. 9 used as a trans-facet screw.

As shown in FIG. 18, the fixation devices 12A, 12B may be used to provide stability without additional hardware. In this example, the fixation device 12A, 12B is used as a trans-facet screw. That is, the fixation device extends through a facet of a first vertebra and into the facet of a second, typically inferior, vertebrae. As in the illustrated embodiment, this procedure is typically (but not necessarily) preformed with bilateral symmetry. Thus, even in the absence of a stabilizing bar tying pedicle screws to adjacent vertebrae or to the sacrum, and in the absence of translaminar screws that can extend through the spinous process, the fixation devices 12A, 12B can be used to stabilize two vertebrae, such as L3 and L4 to each other pending the healing of a fusion. In one embodiment, the body 28 of fixation devices 12A, 12B has a length of approximately 10 mm-30 mm and the diameter of the body is approximately 3 mm to 5.5 mm.

Figure 19:
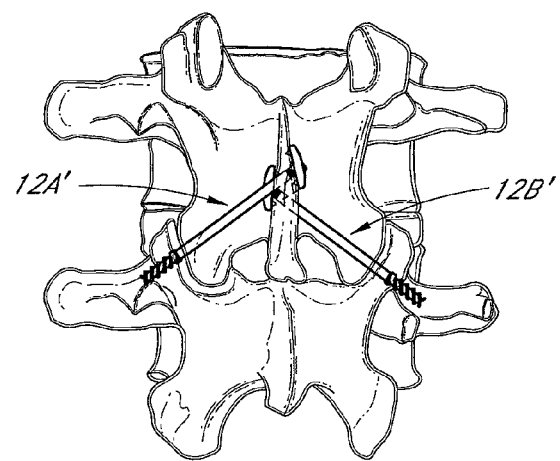
FIG. 19 is a posterior view of a portion of the lumbar spine with the fixation device of FIG. 9 used as a trans-laminar screw.

FIG. 19 illustrates a modified arrangement for spinal fixation in which the fixation devices 12A', 12B' are used as trans-laminar facet screws. As shown in FIG. 19, in this embodiment of use, the fixation device extends through the spinous process and facet of a first vertebra and into the facet of a second, typically inferior, vertebra. As with the previous embodiment, this procedure is typically (but not necessarily) preformed with bilateral symmetry. In one embodiment, the body 28 of fixation devices 12A, 12B has a length of approximately 50 mm-90 mm and the diameter of the body is approximately 4 mm to 5.5 mm.

Figure 20:
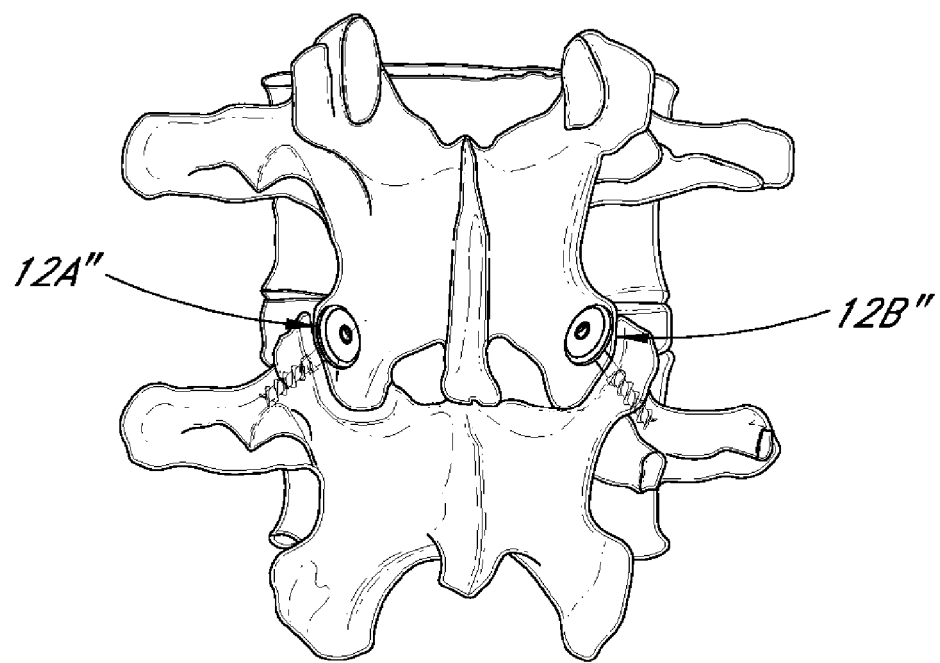
FIG. 20 is a posterior view of a portion of the lumbar spine with the fixation device of FIG. 9 used as a facet-pedicle screw.

FIG. 20 illustrates another modified arrangement for spinal fixation in which the fixation device 12A'', 12B'' is used as a facet-pedical screw (e.g., as used in the Boucher technique). In such an embodiment, the fixation device extends through the facet of a first vertebra and into the pedicle a second, typically inferior, vertebra. As with the previous embodiment, this procedure is typically (but not necessarily) preformed with bilateral symmetry. In such an embodiment, the fixation device 12A, 12B the body 28 is approximately 20-40 millimeters in length and 3.0-5.5 millimeters in diameter.

In the embodiments of FIGS. 18, 19 and 20, the flange of the proximal anchor is typically supported directly against the outer surface of a vertebra. Because the outer surface is typically non-planar and/or the insertion angle of the fixation device is not perpendicular to the outer surface, an angularly fixed flange may contact only a portion of the outer surface. That is, the contact surface of the flange may not sit flush on the outer surface of the vertebra. This may cause the vertebra to crack due to high stress concentrations. This can result in poor fusion rates.

As such, in these applications, the angularly adjustable flanges of the embodiments described with reference to FIGS. 7-15 are particularly advantageous because the flange can rotate with respect to the body and thereby the bone contacting surface may be positioned more closely to the outer surface of the vertebra. This results in more bone contacting surface being utilized and the stress supported by the fixation device is spread out over a larger area of the vertebra. These angularly adjustable flanges may also be used with the spinal cages and rods. In such embodiments, the angle of the body fixation device may be not be perpendicular to the contact surface of the fixation rod or plate. In such situations, the angularly adjustable flange allows the flange to rotate and sit flush against the fixation rod and plate. In the embodiment described with respect to FIGS. 7 and 9, openings may be provided in the flange so that the flange may be coupled to the fixation rod or plate by for example screws or bolts.

In the above embodiments, it may be advantageous to drill a counter bore into the first vertebra for receiving a portion of the proximal anchor. In such embodiments, the counter bore will typically have a diameter that is slightly larger than the outer diameter of the proximal anchor so that the proximal anchor may sit at least partially below the outer surface of the vertebra.

In certain regions of the spine, the dimension transverse to a facet joint and through the adjacent facets is relatively small. In these circumstances, the fixation may desirably include a through bore, opening through the distal cortex of the distal facet. The fixation device described above may be utilized either in a blind hole application, which the distal anchor is buried within the bone, or a through bore application is which the distal helix extends into and potentially through the distal cortex. However, a through bore fixation device such as the fixation device 500 illustrated in FIGS. 21-23 may also be used.

Figure 22:
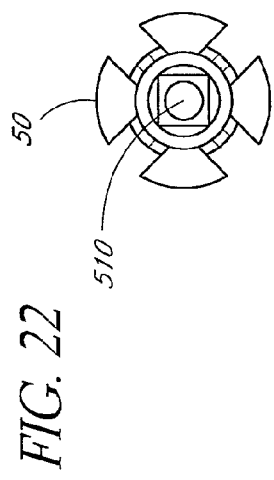
FIG. 22 is a front view of the bone fixation device of FIG. 20.
Figure 21:
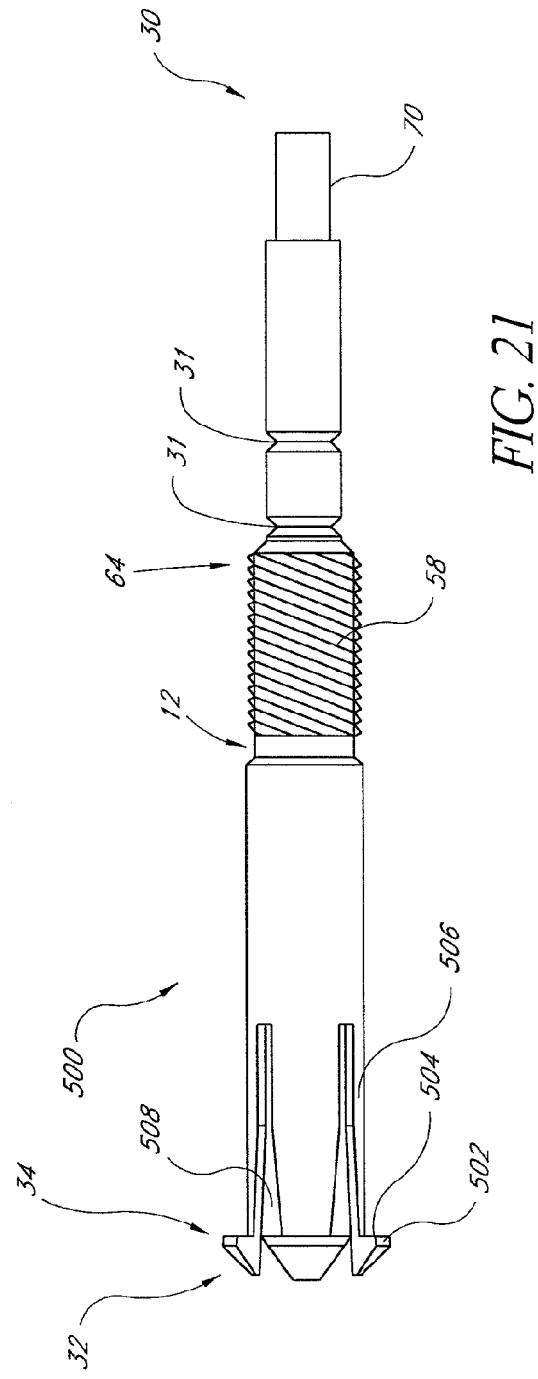
FIG. 21 is a side perspective view of another embodiment of a bone fixation device.
Figure 23:
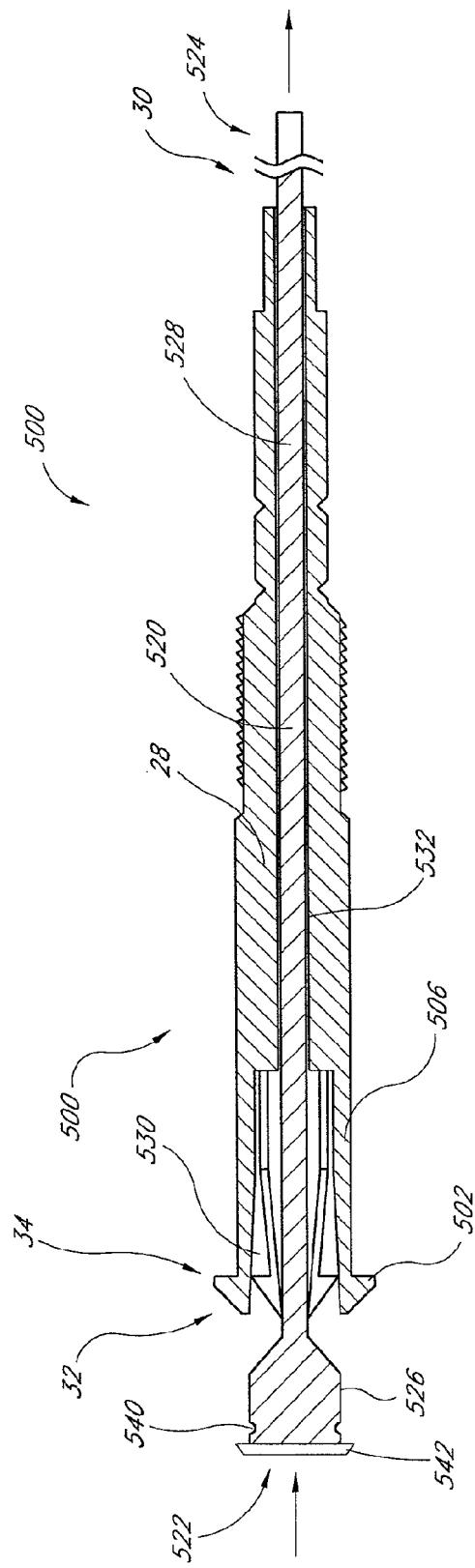
FIG. 23 is a cross-sectional view of the bone fixation device of FIG. 20.

As shown in FIGS. 21-23, the through bore bone fixation device 500 includes a body 28 extending between a proximal end 30 and a distal end 32. The distal end 32 includes a distal anchor 34 which will be described in more detail below. The proximal end 30 may include break points 31. In other embodiments, the proximal end 30 may not include break points 31 or may be used with a pull pin 38 as described above with reference to FIG. 4.

Retention structures 58 are spaced axially along the body 28 between a proximal limit 62 and a distal limit 64. As with the previous embodiments, the retention structures 58 may be configured to interact with a proximal anchor to permit one way ratchet like movement and/or screw-type movement. The body 28 may be used with any of the proximal anchors described above including the angularly adjustable flanges and proximal anchors described above with respect to FIGS. 7-15.

The distal anchor 34 comprises a plurality of friction enhancing or interference fit structures such as ramped extensions or barbs 502, for engaging the distal cortical bone or other surface or interior cancellous bone.

Although the illustrated embodiment includes four barbs 502, oriented at 90° with respect to each other, anywhere from one to about twelve or more barbs 502 may be utilized as will be apparent to those of skill in the art in view of the disclosure herein. The barbs 502 may be radially symmetrically distributed about the longitudinal axis of the body 28. Each barb 502 is provided with a transverse engagement surface 504, for contacting the distal surface of the cortical bone or other structure or surface against which the barb 502 is to anchor. Transverse engagement surfaces 504 may lie on a plane which is transverse to the longitudinal axis of the body 28, or may be inclined with respect to the longitudinal axis of the body 28.

In order to facilitate the radially inward compression of the barbs 502 during the implantation process, followed by radially outward movement of the barbs 502 to engage the distal bone surface, each barb 502 in the illustrated embodiment is carried by a flexible or hinged lever arm 506. Lever arms 506 may be formed by creating a plurality of axial slots 508 in the sidewall of the body. The axial slots 508 cooperate with a central lumen 510 to isolate each barb 502 on a unique lever arm 506. The axial length of the axial slots 508 may be varied, depending upon the desired length over which flexing is desirably distributed, the desired range of lateral motion, and may vary depending upon the desired construction material.

The circumferential width of the slots 508 at the distal end 30 is selected to cooperate with the dimensions of the barbs 502 to permit radial inward deflection of each of the barbs 502 so that the body 26 may be press fit through a predrilled hole having an inside diameter approximately equal to the outside diameter of the pin 28 just proximal to the transverse engagement surfaces 502. For this purpose, each of the slots 508 tapers in circumferential direction width from a relatively larger dimension at the distal end 30 to a relatively smaller dimension at the proximal limit of the axial slot 508.

The fixation device 500 may be used with a locking guide wire 520. The guide wire has a distal end 522 and a proximal end 524. The illustrated guide wire 520 comprises a locking portion 526 that is located at the distal end 522 of the guide wire 520 and an elongated portion 528 that preferably extends from the distal portion 522 to the proximal end 524 of the guide wire 520. The diameter D1 of the elongated portion 528 is generally smaller than the diameter D2 of the locking portion 526. The guide wire 502 can be made from stainless steel, titanium, or any other suitable material.

The locking portion 526 on guidewire 502 can take any of a variety of forms, and accomplish the intended function as will be apparent to those of skill in the art in view of the disclosure herein. For example, a generally cylindrical locking structure, as illustrated, may be used. Alternatively, any of a variety of other configurations in which the cross section is greater than the cross section of the proximal portion 528 may be used. Conical, spherical, or other shapes may be utilized, depending upon the degree of compression desired and the manner in which the locking portion 156 is designed to interfit with the distal end 30 of the pin.

The guide wire 502 is configured such that its proximal end can be threaded through the lumen 510 of the pin 26. With reference to FIG. 22, the lumen 510 preferably comprises a first portion 530 and a second portion 532. The first portion 530 is generally located at the distal end 30 within the region of the lever arms of the pin 26. The second portion 532 preferably extends from the first portion 530 to the proximal end 28 of the pin 28. The inside diameter of the first portion 530 is generally larger than the diameter of the second portion 532. As such, the junction between the first portion 530 and the second portion 532 forms a transverse annular engagement surface 534, which lies transverse to the longitudinal axis of the body 28.

As mentioned above, the guide wire 520 is configured such that its proximal end can be threaded through the lumen 510 of the body 38. As such, the diameter D1 of the elongated portion 528 is less than the diameter of the second portion 530 of the lumen 11. In contrast, the diameter D2 of locking portion 526 preferably is slightly smaller than equal to or larger than the diameter of the first portion 530 and larger than the diameter of the second portion 532. This arrangement allows the locking portion 536 to be retracted proximally into the first portion 530 but prevents the locking portion 536 from passing proximally through the body 28.

In addition, any of a variety of friction enhancing surfaces or surface structures may be provided, to resist distal migration of the locking guidewire 502, post deployment. For example, any of a variety of radially inwardly or radially outwardly directed surface structures may be provided along the length of the locking guidewire 520, to cooperate with a corresponding surface structure on the inside surface of the lumen 510, to removably retain the locking guidewire 520 therein. In the embodiment, a cylindrical groove is provided on the inside surface of the lumen 510 to cooperate with annular ridge 540 on the outside diameter of the locking portion 526 The complementary surface structures may be toleranced such that the locking guidewire or guide pin may be proximally retracted into the lumen 520 to engage the locking structure, but the locking structure provides a sufficient resistance to distal migration of the locking guidewire 502 such that it is unlikely or impossible to become disengaged under normal use. To further resist proximal migration of the 502, the illustrated locking portion 526 also includes an radially outwardly directed flange 542.

In use, after the clinician assesses the bone, selects a bone drill and drills a through hole, the distal end of the guide wire 520 and the distal end 30 of the body 28 are advanced through the through hole until the distal portion 526 and the barbs 502 exit the distal aperture. The proximal anchor may be positioned on the bone fixation device 500 prior to positioning of the pin body 28 in the through hole, or following placement of the pin body 28 within through hole.

The guide wire 520 is preferably thereafter retracted until the distal portion 526 enters, at least partially, the first portion 530 of the pin 26. The proximal anchor 36 can then be rotated or otherwise distally advanced with respect to the body 28 so as to seat the distal anchor 34 snugly against the distal component of the bone or a fixation plate or rod. As such, at least a part of the distal portion 526 of the guide wire 520 becomes locked within the body 28. This prevents the barbs 502 and lever arms 506 from being compressed radially inward and ensures that the barbs 502 remain seated snugly against the distal component of the bone.

Following appropriate tensioning of the proximal anchor, the proximal end of the body 32 and the proximal end of the guide wire 520 are preferably cut off or otherwise removed.

Additional details of the illustrated fixation device including modified embodiments are disclosed in U.S. application Ser. No. 815,263 filed Mar. 22, 2001 entitled Bone Fixation System, the entirety of which is incorporated by reference herein, may also be utilized.

In use, the fixation pin of FIGS. 21-23 may be used in any through bore applications such as between adjacent facets or other structural components of the spine. This includes both the fixation of adjacent bone fragments with or without the attachment of additional hardware such as plates and rods, as has been discussed elsewhere herein. The fixation pin 500 may also be used to engage the distal surface of the proximal cortex, to achieve fixation in the spine.

The fixation devices described above may be made from either conventional bioabsorbable materials or conventional non-absorbable materials, combinations thereof and equivalents thereof. In addition, natural materials such as allografts may be used. Examples of absorbable materials include homopolymers and copolymers of lactide, glycolide, trimethylene carbonate, caprolactone, and p-dioxanone and blends thereof. The following two blends may be useful: 1) the blend of poly(p-dioxanone) and a lactide/glycolide copolymer, as disclosed in U.S. Pat. No. 4,646,741 which is incorporated by reference and (2) the glycolide-rich blend of two or more polymers, one polymer being a high lactide content polymer, and the other being a high glycolide content disclosed in U.S. Pat. No. 4,889,119 which is incorporated by reference. Additional bioabsorbable materials are disclosed in copending application Ser. No. 09/558,057 filed Apr. 26, 2000, the disclosure of which is incorporated in its entirety herein by reference.

The fixation devices may also be made from conventional non-absorbable, biocompatible materials including stainless steel, titanium, alloys thereof, polymers, composites and the like and equivalents thereof. In one embodiment, the distal anchor comprises a metal helix, while the body and the proximal anchor comprise a bioabsorbable material. Alternatively, the distal anchor comprises a bioabsorbable material, and the body and proximal anchor comprise either a bioabsorbable material or a non-absorbable material. As a further alternative, each of the distal anchor and the body comprise a non-absorbable material, connected by an absorbable link. This may be accomplished by providing a concentric fit between the distal anchor and the body, with a transverse absorbable pin extending therethrough. This embodiment will enable removal of the body following dissipation of the pin, while leaving the distal anchor within the bone.

The components of the invention (or a bioabsorbable polymeric coating layer on part or all of the anchor surface), may contain one or more bioactive substances, such as antibiotics, chemotherapeutic substances, angiogenic growth factors, substances for accelerating the healing of the wound, growth hormones, antithrombogenic agents, bone growth accelerators or agents, and the like. Such bioactive implants may be desirable because they contribute to the healing of the injury in addition to providing mechanical support.

In addition, the components may be provided with any of a variety of structural modifications to accomplish various objectives, such as osteoincorporation, or more rapid or uniform absorption into the body. For example, osteoincorporation may be enhanced by providing a micropitted or otherwise textured surface on the components. Alternatively, capillary pathways may be provided throughout the body and collar, such as by manufacturing the anchor and body from an open cell foam material, which produces tortuous pathways through the device. This construction increases the surface area of the device which is exposed to body fluids, thereby generally increasing the absorption rate. Capillary pathways may alternatively be provided by laser drilling or other technique, which will be understood by those of skill in the art in view of the disclosure herein. In general, the extent to which the anchor can be permeated by capillary pathways or open cell foam passageways may be determined by balancing the desired structural integrity of the device with the desired reabsorption time, taking into account the particular strength and absorption characteristics of the desired polymer.

One open cell bioabsorbable material is described in U.S. Pat. No. 6,005,161 as a poly(hydroxy) acid in the form of an interconnecting, open-cell meshwork which duplicates the architecture of human cancellous bone from the iliac crest and possesses physical property (strength) values in excess of those demonstrated by human (mammalian) iliac crest cancellous bone. The gross structure is said to maintain physical property values at least equal to those of human, iliac crest, cancellous bone for a minimum of 90 days following implantation. The disclosure of U.S. Pat. No. 6,005,161 is incorporated by reference in its entirety herein.

In the embodiments described above, it should be appreciated that the distal anchor may be configured to be used with a pre-drilled hole and/or self tapping.

The components of the present invention may be sterilized by any of the well known sterilization techniques, depending on the type of material. Suitable sterilization techniques include heat sterilization, radiation sterilization, such as cobalt 60 irradiation or electron beams, ethylene oxide sterilization, and the like.

The specific dimensions of any of the bone fixation devices of the present invention can be readily varied depending upon the intended application, as will be apparent to those of skill in the art in view of the disclosure herein. Moreover, although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

We claim:

1. A method of treating a fracture of the spine, the method comprising:
   advancing a fixation device that comprises a body having a distal anchor and a proximal anchor towards the spine, the proximal anchor comprises a tubular body and a flange proximal to the tubular body, the proximal anchor comprises a recess entirely within the tubular body;
   inserting the distal anchor of the fixation device into a first bone portion of the spine;
   setting the flange against the first bone portion by moving the proximal anchor distally over retention structures on the body to reduce the distance between the distal anchor and the proximal anchor to compress the fracture of the spine; and engaging a locking element positioned within the recess of the proximal anchor with at least one of the retention structures on the body, wherein the locking element limits proximal movement of the proximal anchor after the proximal anchor is appropriately tensioned.

2. The method of claim 1, wherein the step of advancing a fixation device further comprises rotating the distal anchor.

3. The method of claim 1, wherein the step of moving the proximal anchor distally over retention structures on the body further comprises advancing the proximal anchor over a series of annular ridges and grooves.

4. The method of claim 1, wherein the locking element is an annular ring positioned within the recess of the proximal anchor.

5. The method of claim 1, further comprising moving the locking element radially away from the body.

6. The method of claim 1, wherein the step of moving the proximal anchor distally over retention structures on the body further comprises advancing the proximal anchor over at least 10% the overall length of the fixation device.

7. The method of claim 1, wherein the step of moving the proximal anchor distally over retention structures on the body further comprises advancing the proximal anchor over at least 20% the overall length of the fixation device.

8. The method of claim 1, wherein the step of moving the proximal anchor distally over retention structures on the body further comprises advancing the proximal anchor over at least 50% the overall length of the fixation device.

9. A method of treating a fracture of the spine, the method comprising:

advancing a fixation device that comprises a body having a distal anchor and a proximal anchor towards the spine;

placing the distal anchor of the fixation device into a first bone portion of the spine;

moving the proximal anchor distally over retention structures on the body to reduce the distance between the distal anchor and the proximal anchor to compress the fracture of the spine;

engaging a locking element positioned within a recess of the proximal anchor with at least one retention structure on the body, wherein the locking element limits proximal movement of the proximal anchor after the proximal anchor is appropriately tensioned; and wedging the locking element between the body and a portion of the recess within the proximal anchor to limit proximal movement of the proximal anchor after the proximal anchor is appropriately tensioned.

10. A method of a treating a fracture of the spine, the method comprising:

advancing a fixation device that comprises a body having a distal anchor and a proximal anchor towards the spine, the proximal anchor comprises a tubular body and a proximal flange proximal to the tubular body;

placing the distal anchor of the fixation device into a first bone portion of the spine; and contacting the proximal flange with the first bone portion by moving the proximal anchor distally over retention structures on the body to reduce the distance between the distal anchor and the proximal anchor, such that a ratchet on the proximal anchor engages at least one of the retention structures on the body to compress the fracture and resist proximal movement of the proximal anchor with respect to the body, wherein the ratchet is disposed distal of the proximal flange.

11. The method of claim 10, wherein the step of advancing a fixation device further comprises rotating the distal anchor.

12. The method of claim 10, wherein the step of moving the proximal anchor distally over retention structures on the body further comprises advancing the proximal anchor over a series of annular ridges and grooves.

13. The method of claim 10, wherein the proximal anchor comprises an annular ring positioned within an annular recess of the proximal anchor, and a radially inner surface of the annular ring defines the ratchet.

14. The method of claim 10, wherein the step of moving the proximal anchor distally over retention structures on the body further comprises advancing the proximal anchor over at least 10% the overall length of the fixation device.

15. The method of claim 10, wherein the step of moving the proximal anchor distally over retention structures on the body further comprises advancing the proximal anchor over at least 20% the overall length of the fixation device.

16. The method of claim 10, wherein the step of moving the proximal anchor distally over retention structures on the body further comprises advancing the proximal anchor over at least 50% the overall length of the fixation device.

17. The method of claim 10, further comprising engaging a locking element positioned within a recess of the proximal anchor with at least one retention structure on the body, the recess entirely within the tubular body.

18. The method of claim 17, wherein the locking element comprises a split ring.

19. The method of claim 10, further comprising inserting the tubular body into the portion of the spine.

20. The method of claim 10, further comprising viewing visual indicia on the tubular body to determine the depth of proximal anchor within the portion of the spine.

* * * * *